US010858654B2

(12) United States Patent
Leof et al.

(10) Patent No.: US 10,858,654 B2
(45) Date of Patent: Dec. 8, 2020

(54) POLYPEPTIDE INHIBITORS OF SMAD3 POLYPEPTIDE ACTIVITIES

(71) Applicant: Mayo Foundation for Medical Education and Research, Rochester, MN (US)

(72) Inventors: Edward B. Leof, Rochester, MN (US); Mark C. Wilkes, Plainview, MN (US); Claire E. Repellin, Alameda, CA (US); Jeong-Han Kang, Rochester, MN (US); Xueqian Yin, Rochester, MN (US); Mahefatiana Andrianifahanana, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/184,768

(22) Filed: Nov. 8, 2018

(65) Prior Publication Data

US 2019/0062747 A1    Feb. 28, 2019

Related U.S. Application Data

(62) Division of application No. 15/426,455, filed on Feb. 7, 2017, now Pat. No. 10,144,929.

(60) Provisional application No. 62/354,447, filed on Jun. 24, 2016, provisional application No. 62/297,277, filed on Feb. 19, 2016, provisional application No. 62/295,843, filed on Feb. 16, 2016.

(51) Int. Cl.
| | |
|---|---|
| *A61K 38/16* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C12N 15/113* | (2010.01) |
| *C12N 15/86* | (2006.01) |
| *C07K 14/47* | (2006.01) |
| *A61K 38/04* | (2006.01) |
| *C07K 7/08* | (2006.01) |
| *A61K 38/10* | (2006.01) |
| *C07K 14/00* | (2006.01) |
| *C12N 15/62* | (2006.01) |

(52) U.S. Cl.
CPC ............ *C12N 15/113* (2013.01); *A61K 38/04* (2013.01); *A61K 38/10* (2013.01); *A61K 38/16* (2013.01); *C07K 7/08* (2013.01); *C07K 14/00* (2013.01); *C07K 14/4702* (2013.01); *C07K 14/4703* (2013.01); *C12N 15/62* (2013.01); *C12N 15/86* (2013.01); *C07K 2319/10* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | |
|---|---|---|
| 2011/0224447 A1 | 9/2011 | Bowman et al. |
| 2014/0056811 A1 | 2/2014 | Jacob et al. |
| 2017/0253873 A1 | 9/2017 | Leof et al. |

OTHER PUBLICATIONS

Yarar et al., "SNX9 activities are regulated by multiple phosphoinositides through both PX and BAR domains," Traffic., 9(1):133-146, Jan. 2008.
Yin et al., "Retromer maintains basolateral distribution of the type II TGF-β receptor via the recycling endosome," Mol Biol Cell., 24(14):2285-2298, Jul. 2013.
Aaronson et al., "Isolation of nuclear pore complexes in association with a lamina," Proc Natl Acad Sci U S A., 72(3)::1007-1011, Mar. 1975.
Anders et al., "Chimeric granulocyte/macrophage colonystimulating factor/transforming growth factor-β (TGF-β) receptors define a model system for investigating the role of homomeric and heteromeric receptors in TGF-β signaling," J Biol Chem., 271(36):21758-21766, Sep. 6, 1996.
Andrianifahanana et al., "ERBB receptor activation is required for profibrotic responses to transforming growth factor β," Cancer Res., 70(19):7421-7430, Oct. 1, 2010.
Andrianifahanana et al., "Profibrotic TGF-ß responses require the cooperative action of PDGF and ErbB receptor tyrosine kinases," FASEB J., 27(11):4444-4454, Nov. 2013.
Arima et al., "Cyclodextrin/Dendrimer Conjugates as DNA and Oligonucleotide Carriers," Curr Top Med Chem., 14( 4):465-477, 2014.
Badour et al., "Interaction of the Wiskott-Aldrich syndrome protein with sorting nexin 9 is required for CD28 endocytosis and cosignaling in T cells," Proc Natl Acad Sci USA 104(5):1593-1598, Jan. 30, 2007.
Baumann et al., "The E3 ubiquitin ligase Itch regulates sorting nexin 9 through an unconventional substrate recognition domain," FEBS J., 277(13):2803-2814, Jul. 2010.
Becker-Hapak et al., "TAT-mediated protein transduction into mammalian cells," Methods., 24(3):247-256, 2001.

(Continued)

*Primary Examiner* — Thea D'Ambrosio
(74) *Attorney, Agent, or Firm* — Fish & Richardson P.C.

(57) ABSTRACT

This document provides polypeptide inhibitors of Smad3 polypeptide activities. For example, methods and materials for using polypeptides (e.g., polypeptides designed to include both a cell penetrating amino acid sequence and an amino acid segment of a SH3 domain of a SNX9 polypeptide) to inhibit one or more Smad3 polypeptide activities are provided. This document also provides methods and materials for using RNA interference to treat a disease (e.g., a fibrotic disease) in a mammal (e.g., a human).

12 Claims, 23 Drawing Sheets

Specification includes a Sequence Listing.

(56) References Cited

OTHER PUBLICATIONS

Bendris et al., "SNX9 promotes metastasis by enhancing cancer cell invasion via differential regulation of RhoGTPases," Mol Biol Cell., 27(9):1409-1419, May 1, 2016.
Carlton et al., "Sorting nexins—unifying trends and new perspectives," Traffic., 6(2):75-82, Feb. 2005.
Chacko et al., "Structural basis of heteromeric smad protein assembly in TGF-β signaling," Mol Cell., 15(5):813-823, Sep. 10, 2004.
Chen et al., "Nuclear targeting of transforming growth factor-β-activated Smad complexes," J Biol Chem 280(22):21329-21336, Jun. 3, 2005.
Chikenji et al., "Transforming Growth Factor-0 (TGF-β) Expression is Increased in the Subsynovial Connective Tissues of Patients with Idiopathic Carpal Tunnel Syndrome," J Orthop Res., 32(1):116-122, Jan. 2014.
Childress et al., "Dimerization is required for SH3PX1 tyrosine phosphorylation in response to epidermal growth factor signalling and interaction with ACK2," Biochem J., 394:693-698, 2006.
Cullen., "Endosomal sorting and signalling: an emerging role for sorting nexins," Nat Rev Mol Cell Biol., 9(7):574-582, Jul. 2008.
Daniels et al., "Imatinib mesylate inhibits the profibrogenic activity of TGF-β and prevents bleomycin-mediated lung fibrosis," J Clin Invest., 114(9):1308-1316, Nov. 2004.
Dhande et al., "N-Acetylgalactosamine Block-co-Polycations Form Stable Polyplexes with Plasmids and Promote Liver-Targeted Delivery," Biomacromolecules., 17(3):830-840, 2016.
Di Guglielmo et al., "Distinct endocytic pathways regulate TGF-ß receptor signaling and turnover," Nat Cell Biol., 5(5):410-421, May 2003.
Dislich et al., "Specific amino acids in the BAR domain allow homodimerization and prevent heterodimerization of sorting nexin 33," Biochem J., 433:75-83, 2011.
Elliott et al., "Role of transforming growth factor β in human cancer," J Clin Oncol., 23(9):2078-2093, Mar. 20, 2005.
Ettema et al., "A histological and immunohistochemical study of the subsynovial connective tissue in idiopathic carpal tunnel syndrome," J Bone Joint Surg Am., 86-A(7):1458-1466, Jul. 2004.
Feng et al., "Specificity and versatility in TGF-β signaling through Smads," Annu Rev Cell Dev Biol., 21:659-693, 2005.
Genbank Accession No. NM_016224 (GI No. 525313625), "*Homo sapiens* sorting nexin 9 (SNX9), mRNA," Sep. 3, 2017, 7 pages.
Gingery et al., "TGF-β Signaling Regulates Fibrotic Expression and Activity in Carpal Tunnel Syndrome," J Orthop Res., 32(11):1444-1450, Nov. 2014.
Golan et al., "RNAi therapy targeting KRAS in combination with chemotherapy for locally advanced pancreatic cancer patients," Oncotarget., 6(27):24560-24570, Sep. 15, 2015.
Harrison et al., "Conservation of a glycine-rich region in the prion protein is required for uptake of prion infectivity," J Biol Chem., 285(26):20213-20223, Jun. 25, 2010.
Hayes et al., "TGFB receptor internalization into EEA1-enriched early endosomes: role in signaling to Smad2," J Cell Biol., 158(7)1239-1249, Sep. 30, 2002.
Henley et al., "Dynamin-mediated internalization of caveolae," J Cell Biol., 141(1):85-99, 1988.
Hill., "Nucleocytoplasmic shuttling of Smad proteins," Cell Res., 19(1):36-46, Jan. 2009.
Hoot et al.,"Keratinocyte-specific Smad2 ablation results in increased epithelial-mesenchymal transition during skin cancer formation and progression," J Clin Invest., 118(8):2722-2732, Aug. 2008.
Howe et al., "Transforming growth factor β 1 inhibition of p34cdc2 phosphorylation and histone H1 kinase activity is associated with G1/S-phase growth arrest," Mol Cell Biol., 11(3):1185-1194, Mar. 1991.
Inman et al., "Nucleocytoplasmic shuttling of Smads 2, 3, and 4 permits sensing of TGF-β receptor activity," Mol Cell., 10:283-294, Aug. 2002.
Jang et al., "Glycine-rich region regulates cysteine-rich protein 1 binding to actin cytoskeleton," Biochem Biophys Res Commun., 380(3):484-488, Mar. 13, 2009.
Janknecht et al., "TGF-β-stimulated cooperation of smad proteins with the coactivators CBP/p300," Genes Dev., 12(14):2114-2119, Jul. 15, 1998.
Jin et al., "Requirement of a dynein light chain in TGFβ/Smad3 signaling," J Cell Physiol., 221(3):707-715, Dec. 2009.
Kanasty et al., "Delivery materials for siRNA therapeutics," Nat Mater., 12(11):967-977, Nov. 2013.
Katz et al., "A self-administered hand symptom diagram for the diagnosis and epidemiologic study of carpal tunnel syndrome," J Rheumatol., 17(11):1495-1498, Nov. 1990.
Kauffman et al., "Mechanism Matters: A Taxonomy of Cell Penetrating Peptides," Trends Biochem Sci., 40(12):749-764, Dec. 2015.
Kurisaki et al., "Transforming growth factor-β induces nuclear import of Smad3 in an importin-β and Ran-dependent manner," Mol Biol Cell., 12(4):1079-1091, Apr. 2001.
Labbe et al., "Smad2 and Smad3 positively and negatively regulate TGFβ-dependent transcription through the forkhead DNA-binding protein FAST2," Mol Cell., 2(1):109-120, Jul. 1998.
Lam et al., "Pulmonary delivery of therapeutic siRNA," Adv Drug Deliv Rev., 64(1):1-15, Jan. 2012.
Lee et al., "Therapeutic targets for treating fibrotic kidney diseases," Transl Res., 165(4):512-530, Apr. 2015.
Leonard et al., "Robust colorimetric assays for dynamin's basal and stimulated GTPase activities," Methods Enz., 404:490-503, Feb. 2005.
Lundmark et al., "SNX9—a prelude to vesicle release," J Cell Sci., 122:5-11, 2009.
Mackay et al., "The nucleoporin Nup153 has separable roles in both early mitotic progression and the resolution of mitosis," Mol Biol Cell. 20(6):1652-1660, Mar. 15, 2009.
Massague et al., "Smad transcription factors," Genes Dev., 19(23):2783-2810, Dec. 1, 2005.
Meng et al., "Smad2 protects against TGF-β/Smad3-mediated renal fibrosis," J Am Soc Nephrol., 21(9):1477-1487, 2010.
Moses et al., "Transforming growth factor production by chemically transformed cells," Cancer Res., 41(7):2842-2848, Jul. 1981.
Moustaka et al., "Dynamic control of TGF-β signaling and its links to the cytoskeleton," FEBS Lett., 582(14):2051-2065, Jun. 18, 2008.
Murakami et al., "Enteral siRNA delivery technique for therapeutic gene silencing in the liver via the lymphatic route," Scientific Report., 5(17035), 2015, 13 pages.
Naito et al., "siDirect: highly effective, target-specific siRNA design software for mammalian RNA interference," Nucleic Acids Res., 32(Web Server issue):W124-W129, Jul. 1, 2004.
Napetschnig et al., "Structural and functional analysis of the interaction between the nucleoporin Nup214 and the DEAD-box helicase Ddx19," Proc Natl Acad Sci USA., 106(9):3089-3094, Mar. 3, 2009.
Nicolas et al., "Analysis of Smad nucleocytoplasmic shuttling in living cells," J Cell Sci., 117(Pt 18):4113-4125, Aug. 15, 2004.
Park et al., "SNX18 shares a redundant role with SNX9 and modulates endocytic trafficking at the plasma membrane," J Cell Sci., 123(Pt 10):1742-1750, May 15, 2010.
Parks et al., "Sorting nexin 6, a novel SNX, interacts with the transforming growth factor-β family of receptor serinethreonine kinases," J Biol Chem., 276(22):19332-19339, Jun. 1, 2001.
Rahimi et al., "Distinct roles for mammalian target of rapamycin complexes in the fibroblast response to transforming growth factor-β," Cancer Res., 69(1):84-93, Jan. 1, 2009.
Rahimi et al., "TGF-β signaling: A tale of two responses," J Cell Biochem., 102(3):593-608, Oct. 15, 2007.
Ramot et al., "Preclinical Safety Evaluation in Rats of a Polymeric Matrix Containing an siRNA Drug Used as a Local and Prolonged Delivery System for Pancreatic Cancer Therapy," Toxicol Pathol., 44(6):856-865, Aug. 2016.
Rizzuti et al., "Therapeutic applications of the cell-penetrating HIV-1 Tat peptide," Drug Discov Today., 20(1):76-85, Jan. 2015.

(56) References Cited

OTHER PUBLICATIONS

Roberts et al "The two faces of transforming growth factor β in carcinogenesis," Proc Natl Acad Sci USA., 100(15):8621-8623, Jul. 22, 2003.
Roberts et al., "New class of transforming growth factors potentiated by epidermal growth factors: Isolation from non-neoplastic tissues," Proc Natl Acad Sci USA., 78(9):5339-5343, Sep. 1981.
Ross and Hill., "How the Smads regulate transcription," Int J Biochem Cell Biol., 40(3):383-408, 2008.
Schmierer and Hill., "Kinetic analysis of Smad nucleocytoplasmic shuttling reveals a mechanism for transforming growth factorβ-dependent nuclear accumulation of Smads," Mol Cell Biol., 25(22):9845-9858, Nov. 2005.
Schmierer and Hill., "TGFβ-Smad signal transduction: molecular specificity and functional flexibility," Nat Rev Mol Cell Biol., 8(12):970-982, Dec. 2007.
Schmierer et al., "Mathematical modeling identifies Smad nucleocytoplasmic shuttling as a dynamic signal-interpreting system," Proc Natl Acad Sci U S A., 105(18):6608-6613, May 6, 2008.
Shaw et al., "Identification of a self-association domain in the Ewing's sarcoma protein: a novel function for arginine-glycine-glycine rich motifs," J Biochem., 147(6):885-893, Jun. 1, 2010.
Shin et al., "SNX9 regulates tubular invagination of the plasma membrane through interaction with actin cytoskeleton and dynamin 2," J Cell Sci., 121(Pt 8):1252-1263, Apr. 15, 2008.
Song et al., "An assembly-incompetent mutant establishes a requirement for dynamin self-assembly in clathrin-mediated endocytosis in vivo," Mol Biol Cell.,15(5):2243-2252, May 2004.
Soulet et al., "SNX9 Regulates Dynamin Assembly and is Required for Efficient Clathrin-mediated Endocytosis," Mol Biol Cell., 16(4):2058-2067, Apr. 2005.
Stevens., "AAEM minimonograph #26: the electrodiagnosis of carpal tunnel syndrome. American Association of Electrodiagnostic Medicine," Muscle Nerve., 20(12):1477-1486, Dec. 1997.
Strom et al., "Importin-β-like nuclear transport receptors," Genome Biol., 2(6):reviews3008.1-reviews3008.9, 2001.
Varelas et al., "TAZ controls Smad nucleocytoplasmic shuttling and regulates human embryonic stem-cell self-renewal," Nat Cell Biol., 10(7):837-848,Jul. 2008.
Varga et al., "Transforming growth factor-β as a therapeutic target in systemic sclerosis," Nat Rev Rheumatol., 5(4):200-206, Apr. 2009.
Verges., "Retromer and sorting nexins in development," Front Biosci., 12:3825-3851, May 1, 2007.
Verrecchia et al., "Transforming growth factor-β and fibrosis," World J Gastroenterol., 13(22):3056-3062, Jun. 14, 2007.
Wang et al., "Imatinib mesylate blocks a non-Smad TGFb pathway and reduces fibrogenesis in experimental obstructive nephropathy," FASEB J., 19(1):1-11, Jan. 2005.
Wilkes et al., "Cell-type-specific activation of PAK2 by transforming growth factor-ß independent of Smad2 and Smad3," Mol Cell Biol., 23(23):8878-8889, Dec. 2003.
Wilkes et al., "Sorting nexin 9 differentiates ligand-activated Smad3 from Smad2 for nuclear import and transforming growth factor-β signaling," Mol Biol Cell., 26(21):3879-3891, Nov. 1, 2015.
Worby and Dixon "Sorting out the cellular functions of sorting nexins," Nat Rev Mol Cell Biol., 3(12):919-931, Dec. 2002.
Wu et al., "Crystal structure of a phosphorylated Smad2: Recognition of phosphoserine by the MH2 domain and insights on Smad function in TGF-β signaling," Mol Cell., 8(6):1277-1289, Dec. 2001.
Xiao et al., "Importin β mediates nuclear translocation of Smad 3," J Biol Chem., 275(31):23425-23428, 2000.
Xu et al., "Delivery systems for siRNA drug development in cancer therapy," Asian Journal of Pharmaceutical Sciences., 10(1): 1-12, 2015.
Xu et al., "Distinct domain utilization by Smad3 and Smad4 for nucleoporin interaction and nuclear import," J Biol Chem., 278(43):42569-42577, Oct. 24, 2003.
Xu et al., "Smad2 nucleocytoplasmic shuttling by nucleoporins CAN/Nup214 and Nup153 feeds TGFβ signaling complexes in the cytoplasm and nucleus," Mol Cell., 10:271-282, Aug. 2002.
Xu et al., "MSK is required for nuclear import of TGF-{β}/BMP-activated Smads," J Cell Biol., 178(6):981-994, Sep. 10, 2007.
Xue et al., "Sustained activation of SMAD3/SMAD4 by FOXM1 promotes TGF-β-dependent cancer metastasis," J Clin Invest., 124(2):564-579, Feb. 2014.
Yamanaka et al., "The Effect of a Sortin Nexin 9 peptide, a Smad3 Inhibitor, on Subsynovial Connective Tissue Fibrosis in Carpal Tunnel Syndrome," ORS 2016 Annual Meeting Poster No. 1204., Feb. 22, 2016.
Yao et al., "Preferential utilization of Imp?/8 in nuclear import of Smads," J Biol Chem., 283(33):22867-22874, Aug. 15, 2008.

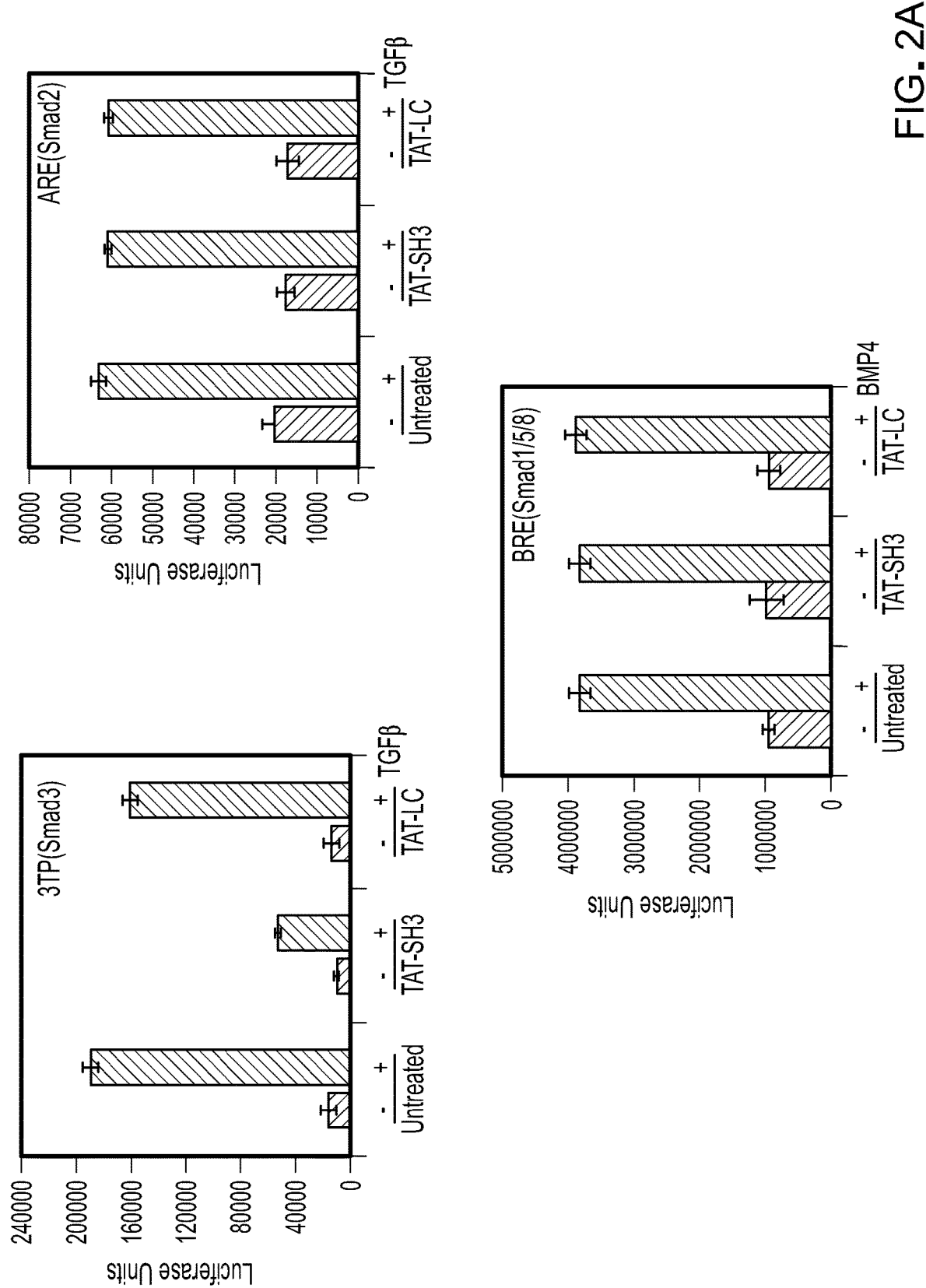

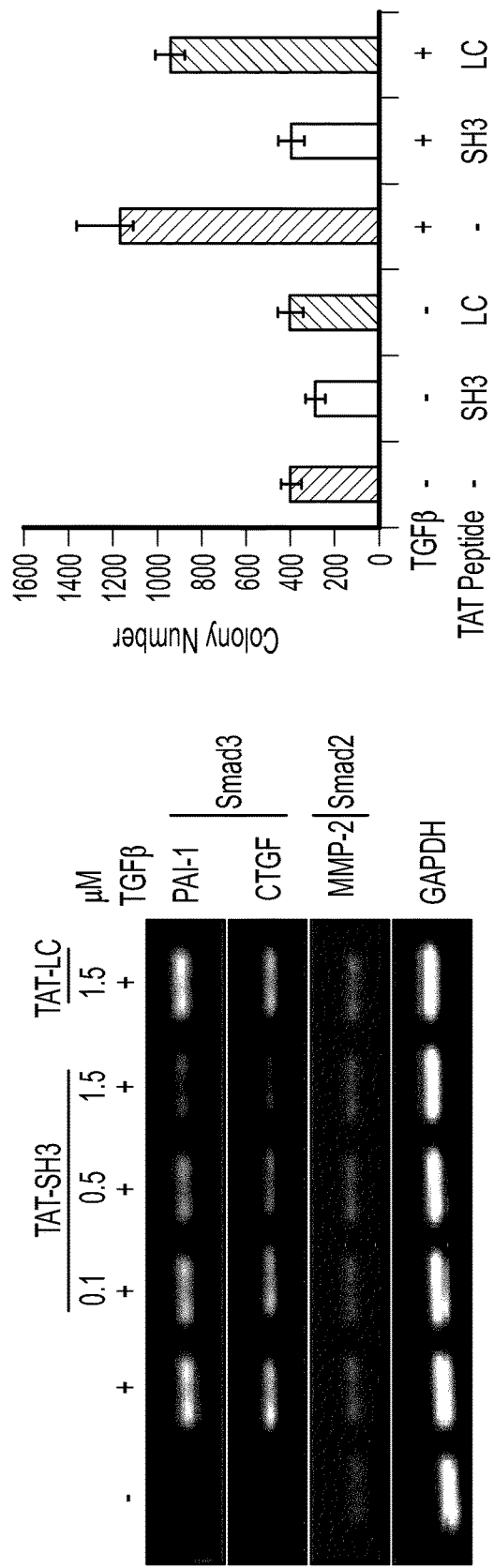
FIG. 2B
FIG. 2C
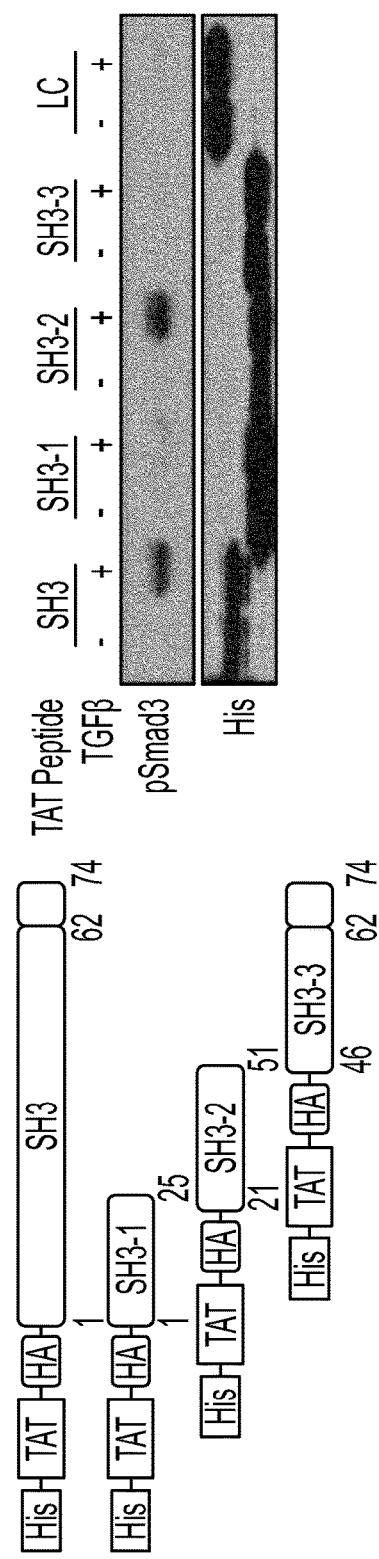
FIG. 3A

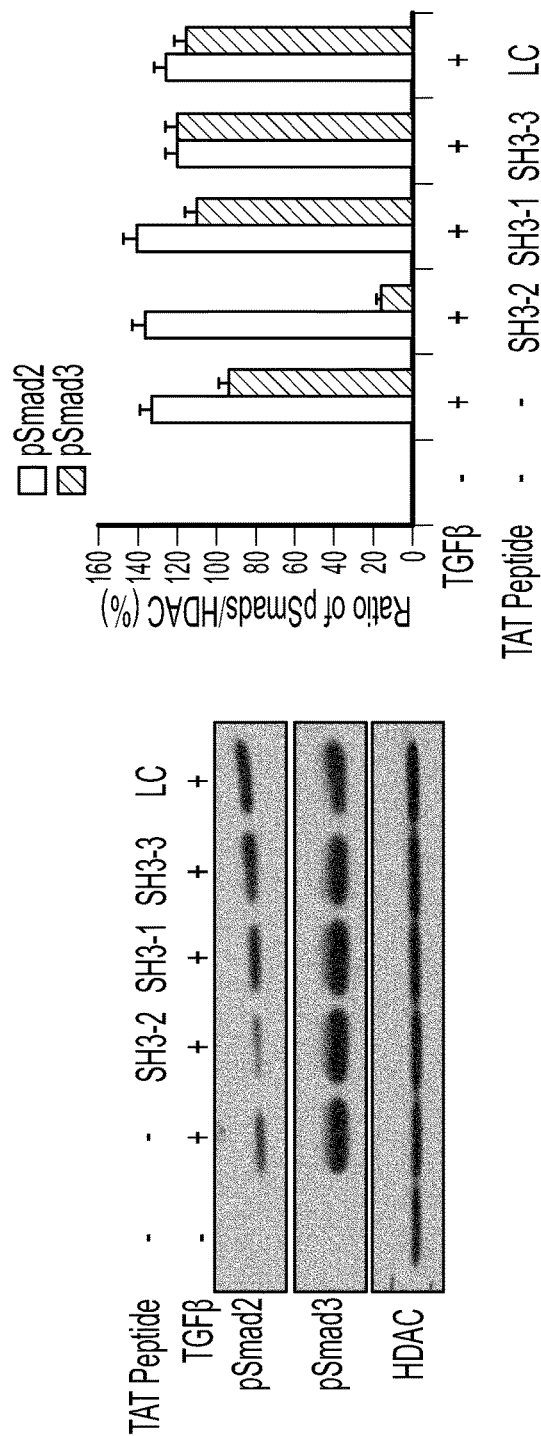
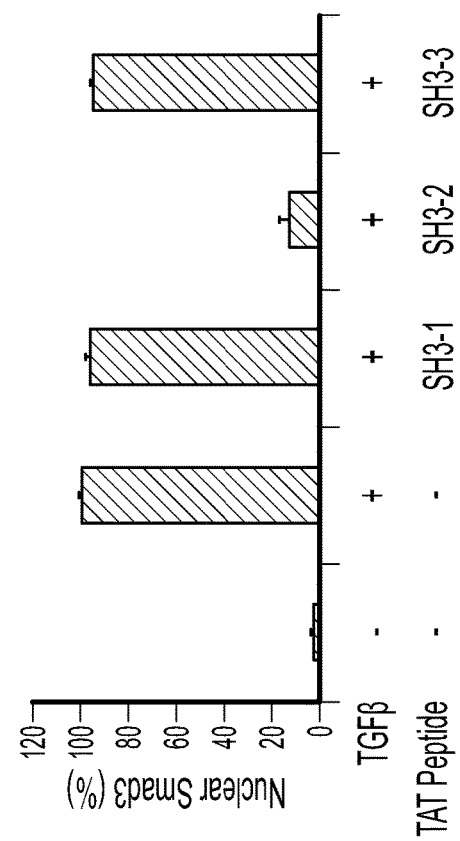
FIG. 3B
FIG. 3C

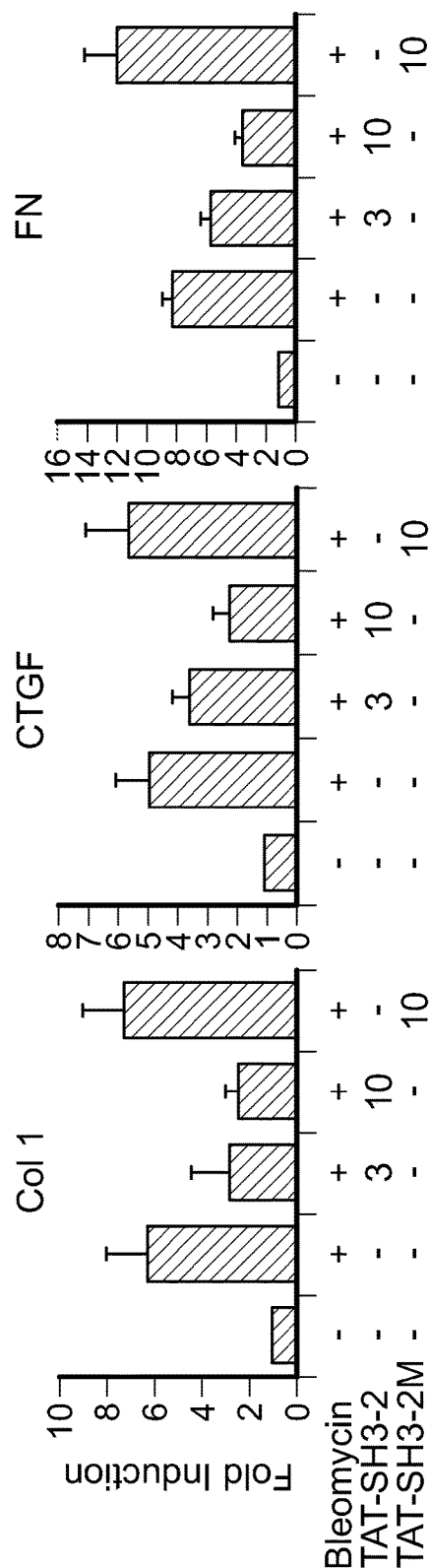
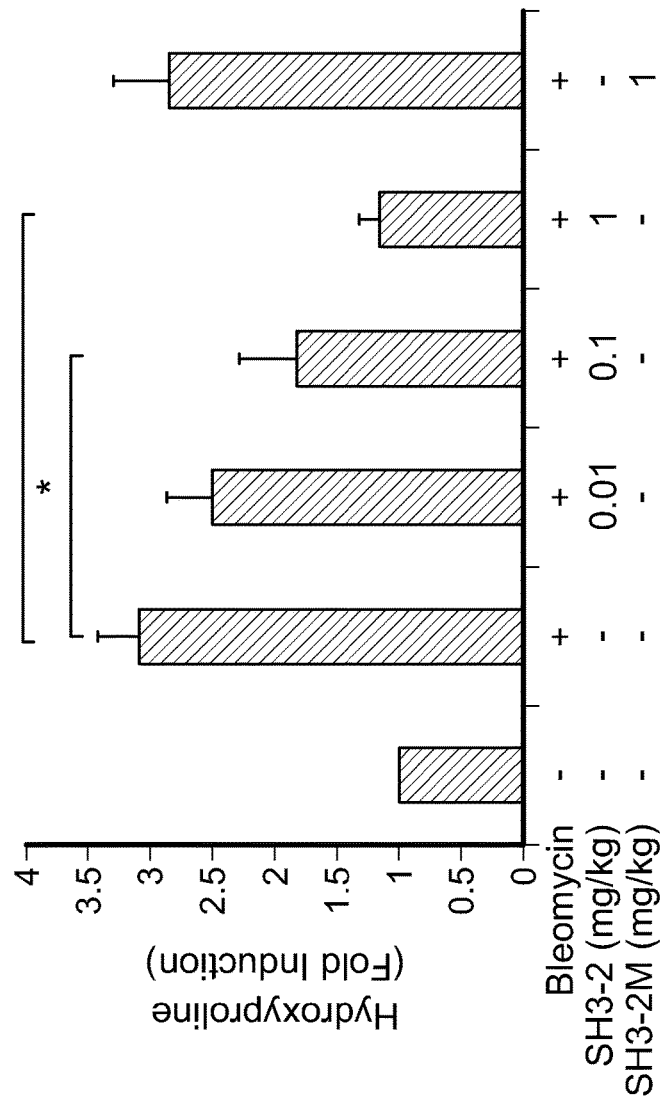
FIG. 5B
FIG. 5C

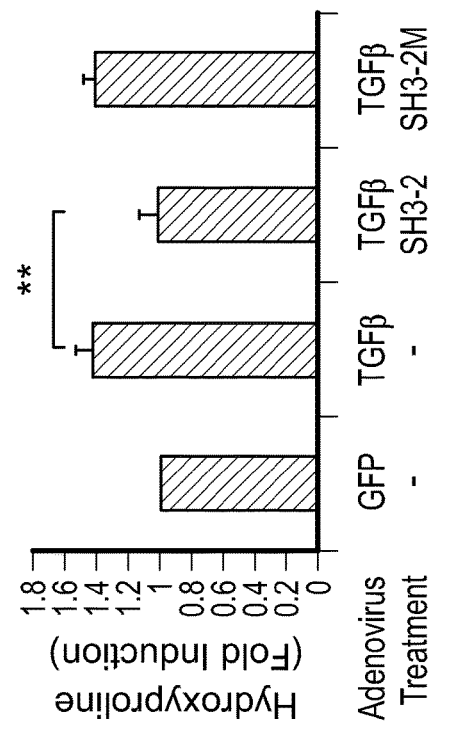
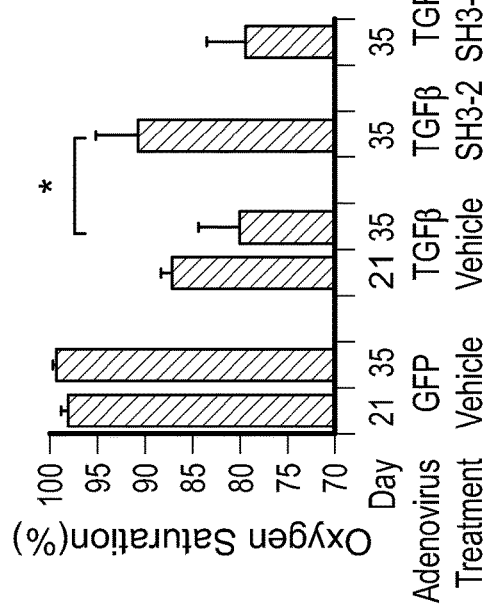
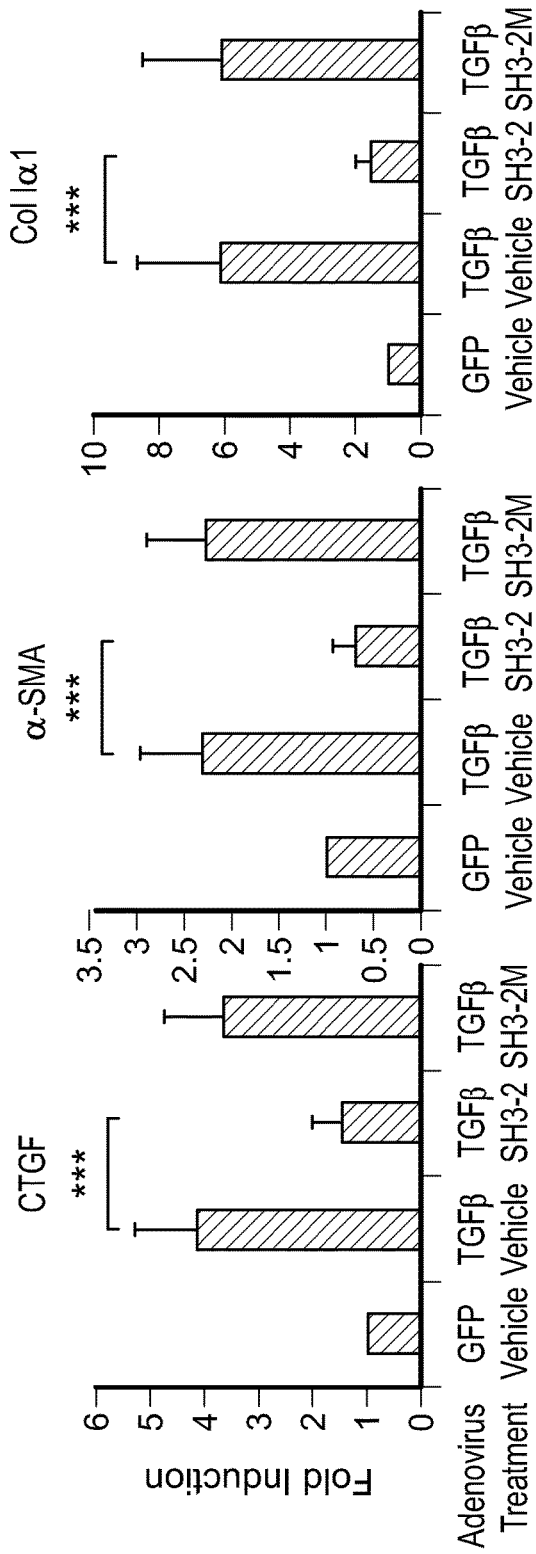
FIG. 13A
FIG. 13B
FIG. 13C

US 10,858,654 B2

SEQUENCE LISTING

<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: Cell penetrating amino acid sequence

<400> SEQUENCE: 1

Gly Tyr Gly Arg Lys Lys Arg Arg Gln Arg Arg Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Cell penetrating amino acid sequence

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Cell penetrating amino acid sequence

<400> SEQUENCE: 3

Arg Arg Arg Arg Arg Arg Arg Arg Arg
1               5

<210> SEQ ID NO 4
<211> LENGTH: 21
<212> TYPE: PRT
<213> ORGANISM: Artificial Sequence
<220> FEATURE:
<223> OTHER INFORMATION: Cell penetrating amino acid sequence

<400> SEQUENCE: 4

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 5
<211> LENGTH: 12
<212> TYPE: PRT
<213> ORGANISM: Artificial Sequence
<220> FEATURE:
<223> OTHER INFORMATION: Cell penetrating amino acid sequence

<400> SEQUENCE: 5

Pro Leu Ile Tyr Leu Arg Leu Leu Arg Gly Gln Phe
1               5                   10

<210> SEQ ID NO 6
<211> LENGTH: 16
<212> TYPE: PRT
<213> ORGANISM: Artificial Sequence
<220> FEATURE:
<223> OTHER INFORMATION: SH3 domain of a SNX9 polypeptide

<400> SEQUENCE: 6

```
Ile Ile Thr Ile Thr Asn Pro Asp Val Gly Gly Gly Trp Leu Glu Gly
1               5                   10                  15
```

<210> SEQ ID NO 7
<211> LENGTH: 31
<212> TYPE: PRT
<213> ORGANISM: Artificial Sequence
<220> FEATURE:
<223> OTHER INFORMATION: SH3 domain of a SNX9 polypeptide

<400> SEQUENCE: 7

```
Thr Val Asn Glu Gly Glu Ile Ile Thr Ile Thr Asn Pro Asp Val Gly
1               5                   10                  15

Gly Gly Trp Leu Glu Gly Arg Asn Ile Lys Gly Glu Arg Gly Leu
            20                  25                  30
```

<210> SEQ ID NO 8
<211> LENGTH: 62
<212> TYPE: PRT
<213> ORGANISM: Artificial Sequence
<220> FEATURE:
<223> OTHER INFORMATION: SH3 domain of a SNX9 polypeptide

<400> SEQUENCE: 8

```
Met Ala Thr Lys Ala Arg Val Met Tyr Asp Phe Ala Ala Glu Pro Gly
1               5                   10                  15

Asn Asn Glu Leu Thr Val Asn Glu Gly Glu Ile Ile Thr Ile Thr Asn
            20                  25                  30

Pro Asp Val Gly Gly Gly Trp Leu Glu Gly Arg Asn Ile Lys Gly Glu
        35                  40                  45

Arg Gly Leu Val Pro Thr Asp Tyr Val Glu Ile Leu Pro Ser
    50                  55                  60
```

<210> SEQ ID NO 9
<211> LENGTH: 60
<212> TYPE: PRT
<213> ORGANISM: Artificial Sequence
<220> FEATURE:
<223> OTHER INFORMATION: polypeptide inhibitor of Smad3

<400> SEQUENCE: 9

```
Gly Tyr Gly Arg Lys Lys Arg Gln Arg Arg Gly Ser Met Ser
1               5                   10                  15

Gly Tyr Pro Tyr Asp Val Pro Asp Tyr Ala Gly Ser Met Thr Val Asn
            20                  25                  30

Glu Gly Glu Ile Ile Thr Ile Thr Asn Pro Asp Val Gly Gly Gly Trp
        35                  40                  45

Leu Glu Gly Arg Asn Ile Lys Gly Glu Arg Gly Leu
    50                  55                  60
```

<210> SEQ ID NO 10
<211> LENGTH: 91
<212> TYPE: PRT
<213> ORGANISM: Artificial Sequence
<220> FEATURE:
<223> OTHER INFORMATION: polypeptide inhibitor of Smad3

<400> SEQUENCE: 10

```
Gly Tyr Gly Arg Lys Lys Arg Gln Arg Arg Gly Ser Met Ser
1               5                   10                  15

Gly Tyr Pro Tyr Asp Val Pro Asp Tyr Ala Gly Ser Met Met Ala Thr
            20                  25                  30
```

```
Lys Ala Arg Val Met Tyr Asp Phe Ala Ala Glu Pro Gly Asn Asn Glu
            35                  40                  45

Leu Thr Val Asn Glu Gly Glu Ile Ile Thr Ile Thr Asn Pro Asp Val
 50                  55                  60

Gly Gly Gly Trp Leu Glu Gly Arg Asn Ile Lys Gly Glu Arg Gly Leu
 65                  70                  75                  80

Val Pro Thr Asp Tyr Val Glu Ile Leu Pro Ser
                 85                  90
```

<210> SEQ ID NO 11
<211> LENGTH: 45
<212> TYPE: PRT
<213> ORGANISM: Artificial Sequence
<220> FEATURE:
<223> OTHER INFORMATION: polypeptide inhibitor of Smad3

<400> SEQUENCE: 11

```
Gly Tyr Gly Arg Lys Lys Arg Arg Gln Arg Arg Gly Ser Met Ser
 1               5                  10                  15

Gly Tyr Pro Tyr Asp Val Pro Asp Tyr Ala Gly Ser Met Ile Ile Thr
                 20                  25                  30

Ile Thr Asn Pro Asp Val Gly Gly Trp Leu Glu Gly
            35                  40                  45
```

<210> SEQ ID NO 12
<211> LENGTH: 76
<212> TYPE: PRT
<213> ORGANISM: Artificial Sequence
<220> FEATURE:
<223> OTHER INFORMATION: polypeptide inhibitor of Smad3

<400> SEQUENCE: 12

```
Gly Tyr Gly Arg Lys Lys Arg Arg Gln Arg Arg Gly Ser Met Ala
 1               5                  10                  15

Thr Lys Ala Arg Val Met Tyr Asp Phe Ala Ala Glu Pro Gly Asn Asn
                 20                  25                  30

Glu Leu Thr Val Asn Glu Gly Glu Ile Ile Thr Ile Thr Asn Pro Asp
            35                  40                  45

Val Gly Gly Gly Trp Leu Glu Gly Arg Asn Ile Lys Gly Glu Arg Gly
 50                  55                  60

Leu Val Pro Thr Asp Tyr Val Glu Ile Leu Pro Ser
 65                  70                  75
```

<210> SEQ ID NO 13
<211> LENGTH: 45
<212> TYPE: PRT
<213> ORGANISM: Artificial Sequence
<220> FEATURE:
<223> OTHER INFORMATION: polypeptide inhibitor of Smad3

<400> SEQUENCE: 13

```
Gly Tyr Gly Arg Lys Lys Arg Arg Gln Arg Arg Gly Ser Thr Val
 1               5                  10                  15

Asn Glu Gly Glu Ile Ile Thr Ile Thr Asn Pro Asp Val Gly Gly Gly
                 20                  25                  30

Trp Leu Glu Gly Arg Asn Ile Lys Gly Glu Arg Gly Leu
            35                  40                  45
```

<210> SEQ ID NO 14
<211> LENGTH: 30

```
<212> TYPE: PRT
<213> ORGANISM: Artificial Sequence
<220> FEATURE:
<223> OTHER INFORMATION: polypeptide inhibitor of Smad3

<400> SEQUENCE: 14

Gly Tyr Gly Arg Lys Lys Arg Arg Gln Arg Arg Gly Ser Ile Ile
1               5                   10                  15

Thr Ile Thr Asn Pro Asp Val Gly Gly Trp Leu Glu Gly
            20                  25                  30

<210> SEQ ID NO 15
<211> LENGTH: 47
<212> TYPE: PRT
<213> ORGANISM: Artificial Sequence
<220> FEATURE:
<223> OTHER INFORMATION: polypeptide inhibitor of Smad3

<400> SEQUENCE: 15

Arg Gln Ile Lys Ile Trp Phe Gln Asn Arg Arg Met Lys Trp Lys Lys
1               5                   10                  15

Thr Val Asn Glu Gly Glu Ile Ile Thr Ile Thr Asn Pro Asp Val Gly
            20                  25                  30

Gly Gly Trp Leu Glu Gly Arg Asn Ile Lys Gly Glu Arg Gly Leu
        35                  40                  45

<210> SEQ ID NO 16
<211> LENGTH: 32
<212> TYPE: PRT
<213> ORGANISM: Artificial Sequence
<220> FEATURE:
<223> OTHER INFORMATION: polypeptide inhibitor of Smad3

<400> SEQUENCE: 16

Arg Gln Ile Lys Ile Trp Phe Gln Asn Arg Arg Met Lys Trp Lys Lys
1               5                   10                  15

Ile Ile Thr Ile Thr Asn Pro Asp Val Gly Gly Trp Leu Glu Gly
            20                  25                  30

<210> SEQ ID NO 17
<211> LENGTH: 71
<212> TYPE: PRT
<213> ORGANISM: Artificial Sequence
<220> FEATURE:
<223> OTHER INFORMATION: polypeptide inhibitor of Smad3

<400> SEQUENCE: 17

Arg Arg Arg Arg Arg Arg Arg Arg Met Ala Thr Lys Ala Arg Val
1               5                   10                  15

Met Tyr Asp Phe Ala Ala Glu Pro Gly Asn Asn Glu Leu Thr Val Asn
            20                  25                  30

Glu Gly Glu Ile Ile Thr Ile Thr Asn Pro Asp Val Gly Gly Trp
        35                  40                  45

Leu Glu Gly Arg Asn Ile Lys Gly Glu Arg Gly Leu Val Pro Thr Asp
    50                  55                  60

Tyr Val Glu Ile Leu Pro Ser
65                  70

<210> SEQ ID NO 18
<211> LENGTH: 40
<212> TYPE: PRT
<213> ORGANISM: Artificial Sequence
<220> FEATURE:
```

<223> OTHER INFORMATION: polypeptide inhibitor of Smad3

<400> SEQUENCE: 18

Arg Arg Arg Arg Arg Arg Arg Arg Thr Val Asn Glu Gly Glu Ile
1               5                   10                  15

Ile Thr Ile Thr Asn Pro Asp Val Gly Gly Gly Trp Leu Glu Gly Arg
            20                  25                  30

Asn Ile Lys Gly Glu Arg Gly Leu
        35                  40

<210> SEQ ID NO 19
<211> LENGTH: 25
<212> TYPE: PRT
<213> ORGANISM: Artificial Sequence
<220> FEATURE:
<223> OTHER INFORMATION: polypeptide inhibitor of Smad3

<400> SEQUENCE: 19

Arg Arg Arg Arg Arg Arg Arg Arg Ile Ile Thr Ile Thr Asn Pro
1               5                   10                  15

Asp Val Gly Gly Gly Trp Leu Glu Gly
            20                  25

<210> SEQ ID NO 20
<211> LENGTH: 83
<212> TYPE: PRT
<213> ORGANISM: Artificial Sequence
<220> FEATURE:
<223> OTHER INFORMATION: polypeptide inhibitor of Smad3

<400> SEQUENCE: 20

Ala Gly Tyr Leu Leu Gly Lys Ile Asn Leu Lys Ala Leu Ala Ala Leu
1               5                   10                  15

Ala Lys Lys Ile Leu Met Ala Thr Lys Ala Arg Val Met Tyr Asp Phe
            20                  25                  30

Ala Ala Glu Pro Gly Asn Asn Glu Leu Thr Val Asn Glu Gly Glu Ile
        35                  40                  45

Ile Thr Ile Thr Asn Pro Asp Val Gly Gly Gly Trp Leu Glu Gly Arg
50                  55                  60

Asn Ile Lys Gly Glu Arg Gly Leu Val Pro Thr Asp Tyr Val Glu Ile
65                  70                  75                  80

Leu Pro Ser

<210> SEQ ID NO 21
<211> LENGTH: 52
<212> TYPE: PRT
<213> ORGANISM: Artificial Sequence
<220> FEATURE:
<223> OTHER INFORMATION: polypeptide inhibitor of Smad3

<400> SEQUENCE: 21

Ala Gly Tyr Leu Leu Gly Lys Ile Asn Leu Lys Ala Leu Ala Ala Leu
1               5                   10                  15

Ala Lys Lys Ile Leu Thr Val Asn Glu Gly Glu Ile Ile Thr Ile Thr
            20                  25                  30

Asn Pro Asp Val Gly Gly Gly Trp Leu Glu Gly Arg Asn Ile Lys Gly
        35                  40                  45

Glu Arg Gly Leu
    50

<210> SEQ ID NO 22
<211> LENGTH: 37
<212> TYPE: PRT
<213> ORGANISM: Artificial Sequence
<220> FEATURE:
<223> OTHER INFORMATION: polypeptide inhibitor of Smad3

<400> SEQUENCE: 22

```
Ala Gly Tyr Leu Leu Gly Lys Ile Asn Leu Lys Ala Leu Ala Ala Leu
1               5                   10                  15
Ala Lys Lys Ile Leu Ile Ile Thr Ile Thr Asn Pro Asp Val Gly Gly
            20                  25                  30
Gly Trp Leu Glu Gly
        35
```

<210> SEQ ID NO 23
<211> LENGTH: 74
<212> TYPE: PRT
<213> ORGANISM: Artificial Sequence
<220> FEATURE:
<223> OTHER INFORMATION: polypeptide inhibitor of Smad3

<400> SEQUENCE: 23

```
Pro Leu Ile Tyr Leu Arg Leu Leu Arg Gly Gln Phe Met Ala Thr Lys
1               5                   10                  15
Ala Arg Val Met Tyr Asp Phe Ala Ala Glu Pro Gly Asn Asn Glu Leu
            20                  25                  30
Thr Val Asn Glu Gly Glu Ile Ile Thr Ile Thr Asn Pro Asp Val Gly
        35                  40                  45
Gly Gly Trp Leu Glu Gly Arg Asn Ile Lys Gly Glu Arg Gly Leu Val
    50                  55                  60
Pro Thr Asp Tyr Val Glu Ile Leu Pro Ser
65                  70
```

<210> SEQ ID NO 24
<211> LENGTH: 43
<212> TYPE: PRT
<213> ORGANISM: Artificial Sequence
<220> FEATURE:
<223> OTHER INFORMATION: polypeptide inhibitor of Smad3

<400> SEQUENCE: 24

```
Pro Leu Ile Tyr Leu Arg Leu Leu Arg Gly Gln Phe Thr Val Asn Glu
1               5                   10                  15
Gly Glu Ile Ile Thr Ile Thr Asn Pro Asp Val Gly Gly Gly Trp Leu
            20                  25                  30
Glu Gly Arg Asn Ile Lys Gly Glu Arg Gly Leu
        35                  40
```

<210> SEQ ID NO 25
<211> LENGTH: 28
<212> TYPE: PRT
<213> ORGANISM: Artificial Sequence
<220> FEATURE:
<223> OTHER INFORMATION: polypeptide inhibitor of Smad3

<400> SEQUENCE: 25

```
Pro Leu Ile Tyr Leu Arg Leu Leu Arg Gly Gln Phe Ile Ile Thr Ile
1               5                   10                  15
Thr Asn Pro Asp Val Gly Gly Gly Trp Leu Glu Gly
            20                  25
```

```
<210> SEQ ID NO 26
<211> LENGTH: 19
<212> TYPE: RNA
<213> ORGANISM: Artificial Sequence
<220> FEATURE:
<223> OTHER INFORMATION: siRNA molecule targeting human SNX9

<400> SEQUENCE: 26
gcugcugaac cuggaaaua                                                    19

<210> SEQ ID NO 27
<211> LENGTH: 19
<212> TYPE: RNA
<213> ORGANISM: Artificial Sequence
<220> FEATURE:
<223> OTHER INFORMATION: siRNA molecule targeting human SNX9

<400> SEQUENCE: 27
gguucccaca gacuacguu                                                    19

<210> SEQ ID NO 28
<211> LENGTH: 19
<212> TYPE: RNA
<213> ORGANISM: Artificial Sequence
<220> FEATURE:
<223> OTHER INFORMATION: siRNA molecule targeting human SNX9

<400> SEQUENCE: 28
ccaaagaaag aucuccauu                                                    19

<210> SEQ ID NO 29
<211> LENGTH: 19
<212> TYPE: RNA
<213> ORGANISM: Artificial Sequence
<220> FEATURE:
<223> OTHER INFORMATION: siRNA molecule targeting human SNX9

<400> SEQUENCE: 29
gcacucacaa gggagcaau                                                    19

<210> SEQ ID NO 30
<211> LENGTH: 21
<212> TYPE: RNA
<213> ORGANISM: Artificial Sequence
<220> FEATURE:
<223> OTHER INFORMATION: siRNA molecule targeting human SNX9

<400> SEQUENCE: 30
aacagucgug cuaguuccuc a                                                 21

<210> SEQ ID NO 31
<211> LENGTH: 21
<212> TYPE: RNA
<213> ORGANISM: Artificial Sequence
<220> FEATURE:
<223> OTHER INFORMATION: siRNA molecule targeting human SNX9

<400> SEQUENCE: 31
uaagcacuuu gacugguuau u                                                 21

<210> SEQ ID NO 32
<211> LENGTH: 19
<212> TYPE: RNA
<213> ORGANISM: Artificial Sequence
<220> FEATURE:
<223> OTHER INFORMATION: siRNA molecule targeting human SNX9

<400> SEQUENCE: 32
```

```
gggacuuugu agagaauuu                                                19
```

<210> SEQ ID NO 33
<211> LENGTH: 15
<212> TYPE: PRT
<213> ORGANISM: Artificial Sequence
<220> FEATURE:
<223> OTHER INFORMATION: TAT-SNX9(SH3) fusion polypeptide

<400> SEQUENCE: 33

```
Thr Val Asn Glu Gly Glu Ile Ile Thr Ile Thr Asn Pro Asp Val
1               5                   10                  15
```

<210> SEQ ID NO 34
<211> LENGTH: 16
<212> TYPE: PRT
<213> ORGANISM: Artificial Sequence
<220> FEATURE:
<223> OTHER INFORMATION: TAT-SNX9(SH3) fusion polypeptide

<400> SEQUENCE: 34

```
Ile Ile Thr Ile Thr Asn Pro Asp Val Gly Gly Gly Trp Leu Glu Gly
1               5                   10                  15
```

<210> SEQ ID NO 35
<211> LENGTH: 15
<212> TYPE: PRT
<213> ORGANISM: Artificial Sequence
<220> FEATURE:
<223> OTHER INFORMATION: TAT-SNX9(SH3) fusion polypeptide

<400> SEQUENCE: 35

```
Gly Gly Trp Leu Glu Gly Arg Asn Ile Lys Gly Glu Arg Gly Leu
1               5                   10                  15
```

<210> SEQ ID NO 36
<211> LENGTH: 78
<212> TYPE: PRT
<213> ORGANISM: Artificial Sequence
<220> FEATURE:
<223> OTHER INFORMATION: polypeptide inhibitor of Smad3

<400> SEQUENCE: 36

```
Arg Gln Ile Lys Ile Trp Phe Gln Asn Arg Arg Met Lys Trp Lys Lys
1               5                   10                  15

Met Ala Thr Lys Ala Arg Val Met Tyr Asp Phe Ala Ala Glu Pro Gly
                20                  25                  30

Asn Asn Glu Leu Thr Val Asn Glu Gly Glu Ile Ile Thr Ile Thr Asn
            35                  40                  45

Pro Asp Val Gly Gly Gly Trp Leu Glu Gly Arg Asn Ile Lys Gly Glu
        50                  55                  60

Arg Gly Leu Val Pro Thr Asp Tyr Val Glu Ile Leu Pro Ser
65                  70                  75
```

<210> SEQ ID NO 37
<211> LENGTH: 14
<212> TYPE: PRT
<213> ORGANISM: Artificial Sequence
<220> FEATURE:
<223> OTHER INFORMATION: Cell penetrating amino acid sequence

<400> SEQUENCE: 37

```
Gly Tyr Gly Arg Lys Lys Arg Arg Gln Arg Arg Arg Gly Ser
1               5                   10
```

POLYPEPTIDE INHIBITORS OF SMAD3 POLYPEPTIDE ACTIVITIES

CROSS-REFERENCE TO RELATED APPLICATIONS

This application is a divisional of U.S. application Ser. No. 15/426,455, filed Feb. 7, 2017 (now U.S. Pat. No. 10,144,929), which claims the benefit of U.S. Provisional Application Ser. No. 62/354,447, filed Jun. 24, 2016, U.S. Provisional Application Ser. No. 62/297,277, filed Feb. 19, 2016, and U.S. Provisional Application Ser. No. 62/295,843, filed Feb. 16, 2016. The disclosures of the prior applications are considered part of (and are incorporated by reference in) the disclosure of this application.

STATEMENT AS TO FEDERALLY SPONSORED RESEARCH

This invention was made with government support under GM055816 and GM054200, awarded by the National Institutes of Health. The government has certain rights in the invention.

BACKGROUND

1. Technical Field

This document relates to polypeptide inhibitors of Smad3 polypeptide activities. For example, this document provides methods and materials for using polypeptides (e.g., polypeptides designed to include both a cell penetrating amino acid sequence and an amino acid segment of a SH3 domain of a SNX9 polypeptide) to inhibit one or more Smad3 polypeptide activities. This document also relates to methods and materials for using RNA interference to treat a disease (e.g., a fibrotic disease) in a mammal (e.g., a human).

2. Background Information

Transforming growth factor beta (TGFβ) is a 25 kDa polypeptide that regulates a variety of cellular processes including matrix deposition, mitosis, development, differentiation, and apoptosis. The primary intracellular mediators of TGFβ action are the Smad proteins, although non-Smad pathways have been reported, often in a cell-type specific context. Three general categories of Smad proteins were identified: receptor-regulated Smads (R-Smads; Smads2 and 3 for TGFβ or Activin and Smads1, 5, and 8 for BMPs); common-mediator Smad (Co-Smad; Smad4); and inhibitory Smads (I-Smads; Smads6 and 7). The R- and Co-Smad proteins shuttle continuously between the nucleus and cytoplasm in unstimulated cells as well as in the presence of TGFβ.

SUMMARY

This document provides polypeptide inhibitors of Smad3 polypeptide activities. For example, this document provides methods and materials for using polypeptides (e.g., polypeptides designed to include both a cell penetrating amino acid sequence and an amino acid segment of a SH3 domain of a SNX9 polypeptide) to inhibit one or more Smad3 polypeptide activities.

This document also provides methods and materials for using RNA interference to treat a disease (e.g., a fibrotic disease) in a mammal (e.g., a human). For example, small interfering RNA (siRNA) or short hairpin RNA (shRNA) can be designed to target SNX9 nucleic acid and trigger RNA interference against SNX9 nucleic acid expression. Administration of such siRNA or shRNA (or compositions containing or configured to express such siRNAs or shRNAs) can result in a reduced level of SNX9 polypeptide expression within a mammal. In some cases, siRNA or shRNA designed to target SNX9 nucleic acid and trigger RNA interference against SNX9 nucleic acid expression (or compositions containing or configured to express such siRNAs or shRNAs) can be used to treat a disease such as carpal tunnel syndrome, lung, kidney, and/or liver fibrosis, glomerulosclerosis, cirrhosis, vascular restenosis, radiation-induced fibrosis, multiple sclerosis, traumatic brain injury, proliferative vitreoretinopathy, ocular capsule injury, or scleroderma.

In general, one aspect of this document features a polypeptide comprising, or consisting essentially of, a cell penetrating amino acid sequence and an amino acid segment of a SH3 domain of a SNX9 polypeptide, wherein the amino acid segment is less than 45 amino acid residues (e.g., from about 15 to about 40 amino acid residues) in length. The cell penetrating amino acid sequence can be an amino acid sequence set forth in Table 1. The amino acid segment can be an amino acid sequence set forth in Table 2. The polypeptide can comprise an amino acid sequence set forth in Table 3.

In another aspect, this document features a nucleic acid molecule encoding a polypeptide comprising, or consisting essentially of, a cell penetrating amino acid sequence and an amino acid segment of a SH3 domain of a SNX9 polypeptide, wherein the amino acid segment is less than 45 amino acid residues (e.g., from about 15 to about 40 amino acid residues) in length. The cell penetrating amino acid sequence can be an amino acid sequence set forth in Table 1. The amino acid segment can be an amino acid sequence set forth in Table 2. The polypeptide can comprise an amino acid sequence set forth in Table 3.

In another aspect, this document features a host cell comprising a nucleic acid molecule encoding a polypeptide comprising, or consisting essentially of, a cell penetrating amino acid sequence and an amino acid segment of a SH3 domain of a SNX9 polypeptide, wherein the amino acid segment is less than 45 amino acid residues (e.g., from about 15 to about 40 amino acid residues) in length. The cell penetrating amino acid sequence can be an amino acid sequence set forth in Table 1. The amino acid segment can be an amino acid sequence set forth in Table 2. The polypeptide can comprise an amino acid sequence set forth in Table 3.

In another aspect, this document features a method for treating fibrosis in a mammal. The method comprises, or consists essentially of, administering a composition comprising an siRNA or shRNA molecule, or a nucleic acid encoding the siRNA or shRNA molecule, to the mammal, wherein the siRNA or shRNA molecule targets SNX9 nucleic acid and triggers RNA interference against expression of the SNX9 nucleic acid, and wherein the severity of the fibrosis is reduced following the administering step. The mammal can be a human. The composition can comprise the siRNA molecule. The composition can comprise the shRNA molecule. The composition can comprise nucleic acid encoding the siRNA molecule. The composition can comprise nucleic acid encoding the shRNA molecule. The nucleic acid can be a viral vector. The SNX9 nucleic acid can be human SNX9 nucleic acid. The severity of the fibrosis can be reduced by at least 25 percent following the administering step. The severity of the fibrosis can be reduced by at least 50 percent following the administering step. The severity of the fibrosis can be reduced by at least 75 percent following the administering step. The fibrosis can be lung fibrosis. The fibrosis can be liver fibrosis. The fibrosis can be kidney fibrosis.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2C. TAT-SH3 inhibits Smad3-dependent responses. (A) AKR-2B cells were transiently transfected with a Smad3 (3TP), Smad2 (ARE), or Smad1/5/8 (BRE) reporter construct, and luciferase activity determined following 12 hours incubation in the absence (−) or presence (+) of the indicated ligand (5 ng/mL TGFβ; 10 ng/mL BMP4) or TAT-SNX9(SH3) fusion polypeptide (1.5 µM). Data represent the mean+/−SEM of three experiments. (B) RT-PCR analysis of Smad3 (PAI-1 and CTGF) and Smad2 (MMP2) responsive gene following 24 hour treatment of AKR-2B cells with the indicated concentration of TAT-SNX9(SH3) fusion polypeptide or 5 ng/mL TGFβ. Loading was verified by GAPDH expression. (C) Soft agar colony formation was performed following seven days growth in the presence (+) or absence (−) of TGFβ (10 ng/mL) or the indicated TAT-SNX9(SH3) fusion polypeptide (1.5 µM). Data reflects the mean+/−sd of triplicate wells from three experiments.

FIGS. 3A-3E. Inhibition of Smad3 signaling by a defined region of the SH3 domain in SNX9. (A) Cartoon depicting constructs used for His pull down assays. AKR-2B lysates were incubated with the indicated TAT-SNX9(SH3) fusion polypeptide and immunoblotted for bound pSmad3 or total TAT-SNX9(SH3) fusion polypeptide (His). (B) Nuclear fractions were prepared and assessed as in FIG. 1B following transduction with the indicated TAT-SNX9(SH3) fusion polypeptide (Left). Quantitation (mean+/−sd) of nuclear pSmad2 or pSmad3 from 2 experiments (Right). (C) Immunofluorescence of nuclear Smad3 was determined as in FIG. 1C from 30 cells in each of two experiments in the absence (−) or presence (+) of 5 ng/mL TGFβ and the indicated TAT-SNX9(SH3) fusion polypeptide (1.5 µM). (D) qPCR of Smad3 (PAI-1 and CTGF) and Smad2 (Goosecoid and Furin) responsive genes following 24 hours in the absence (−) or presence (+) of TGFβ (5 ng/mL), SB431542 (10 µM; TβRI inhibitor), or the indicated TAT-SNX9(SH3) fusion polypeptide. Data reflect mean+/−sd from three experiments. (E) TGFβ (10 ng/mL) stimulated soft agar colony formation in the absence or presence of the indicated TAT-SNX9(SH3) fusion polypeptide (1.5 µM) or SB431542 (10 µM). Data reflects the mean+/−sd of triplicate wells from three experiments.

FIGS. 5A-5D. Bleomycin (BLM)-induced lung remodeling is attenuated by TAT-SH3-2. (A) Hematoxylin and Eosin (H&E), Masson's Trichrome (MT), or fibronectin (anti-fibronectin and Hematoxylin) staining of representative paraffin-embedded lung sections from Control (saline treated) or mice challenged with BLM for 28 days and treated daily with 0.5 mg/kg TAT-SH3-2 or TAT-SH3-2M beginning 14 days following initial BLM insult (×8). (B) qPCR of the indicated genes (CoII, collagen 1; CTGF, connective tissue growth factor; FN, fibronectin) in murine lung tissue harvested on day 28 from mice challenged with BLM (+) or saline (−) and treated daily with vehicle (−; methocel/saline) or the indicated amount (µg) of TAT-SH3-2 or TAT-SH3-2M as in (A). Data reflect mean+/−sd of n=4. (C) Mice were treated with saline or BLM as in (A) and on day 14 administered daily vehicle (−) or the indicated concentration of TAT peptide. Animals were sacrificed on day 28, and hydroxyproline content was determined as described herein. Data reflect mean+/−sd of n=3. *P<0.005, **P<0.002. (D) Mice were treated as in (C), and qPCR of the indicated genes (Col Iα1 (collagen Iα1); CTGF (connective tissue growth factor); and FN (fibronectin)) were assessed in lung tissue harvested on day 28. Data reflect mean+/−sd of n=5. *P<0.005, **P<0.001.

FIGS. 13A-13C. Mice were infected with $1×10^8$ pfu adenovirus particles expressing control (GFP) or active TGFβ by tracheal instillation. On day 21, all animals began daily treatment with either vehicle (methocel/saline) or 1 mg/kg of the indicated TAT polypeptide. (A) On days 21 and 35, peripheral blood oxygen was determined. (B and C) Mice were sacrificed on day 39 and processed for lung hydroxyproline content (B) or qPCR expression of the indicated genes (C) (CTGF, connective tissue growth factor; α-SMA, alpha smooth muscle actin; Col Iα1, collagen Iα1). For panels A-C, data reflect mean+/−SEM of n=8 and n=16 for adenovirus-GFP and adenovirus-TGFβ, respectively. *P<0.05, P<0.001, *P<0.0005.

DETAILED DESCRIPTION

Figure 1A:
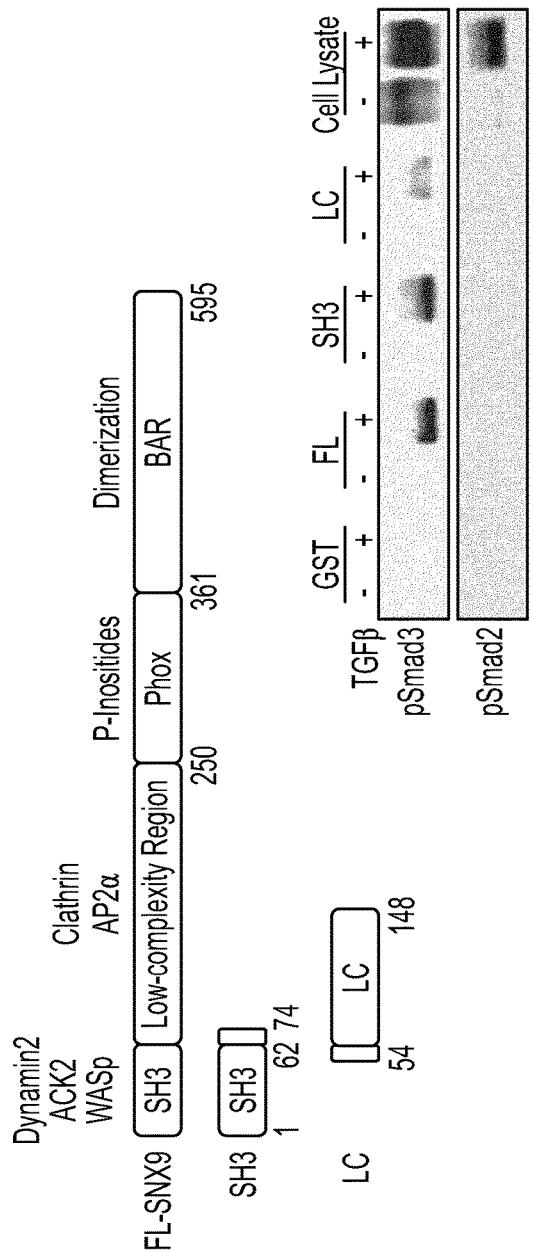
FIGS. 1A-1C. SH3 domain of sorting nexin 9 (SNX9) specifically binds pSmad3 and prevents nuclear import. (A) Cartoon depicting domains in full length (FL) SNX9 and constructs used for GST pull down assays. Lysates from AKR-2B cells untreated (−) or stimulated (+) for 45 minutes with 5 ng/mL TGFβ were incubated with GST beads or the indicated fusion polypeptides immobilized on GST beads. Bound polypeptides were eluted and assessed by Western analysis for pSmad3 or pSmad2. Cell lysate reflects signal obtained from 10 µg total protein. (B) AKR-2B cells were transduced for 90 minutes with the indicated concentrations of the TAT-SNX9(SH3) fusion polypeptides. Following washing and 1 hour TGFβ (5 ng/mL) treatment, nuclear fractions were isolated, and Western blotted for pSmad2, pSmad3, or histone deacetylase 1 (HDAC) (Left). Quantitation of nuclear pSmads was performed with Image J software and represents the mean+/−sd of two experiments (Right). (C) AKR-2B cells were transduced as in (B) with TAT-SH3 or TAT-LC (1.8 µM) and treated+/−TGFβ (5 ng/mL) for 1 hour. Immunofluorescence for Smad3 or the HA-tagged TAT-SNX9(SH3) fusion polypeptide was performed, and nuclei were stained with DAPI (Left panels). Quantitation of nuclear Smad3 from 30 cells in each of two experiments (Right).

This document provides polypeptide inhibitors of Smad3 polypeptide activities. For example, this document provides methods and materials for using polypeptides (e.g., polypeptides designed to include both a cell penetrating amino acid sequence and an amino acid segment of a SH3 domain of a SNX9 polypeptide) to inhibit one or more Smad3 polypeptide activities. In some cases, a polypeptide having both a cell penetrating amino acid sequence and an amino acid segment of a SH3 domain of a SNX9 polypeptide can be designated a TAT-SNX9(SH3) fusion polypeptide.

Any appropriate cell penetrating amino acid sequence can be used to make a polypeptide described herein. For example, the amino acid sequences set forth in Table 1 can be used as a cell penetrating amino acid sequence. Other examples include those described elsewhere (e.g., Kauffman et al., *Trends Biochem. Sci.*, 40:749-64 (2015)).

In some cases, a cell penetrating amino acid sequence can range in length from about 9 amino acid residues to about 30 amino acid residues (e.g., from about 9 amino acid residues to about 25 amino acid residues, from about 9 amino acid residues to about 20 amino acid residues, from about 10 amino acid residues to about 30 amino acid residues, from about 10 amino acid residues to about 25 amino acid residues, from about 10 amino acid residues to about 20 amino acid residues, or from about 12 amino acid residues to about 20 amino acid residues).

TABLE 1

Cell penetrating amino acid sequences.

| Amino acid sequence | SEQ ID NO: |
|---|---|
| GYGRKKRRQRRR | 1 |
| RQIKIWFQNRRMKWKK | 2 |
| RRRRRRRRR | 3 |
| AGYLLGKINLKALAALAKKIL | 4 |
| PLIYLRLLRGQF | 5 |

Any appropriate amino acid segment of a SH3 domain of a SNX9 polypeptide can be used to make a polypeptide described herein. For example, an amino acid sequence set forth in Table 2 can be used as an amino acid segment of a SH3 domain of a SNX9 polypeptide to make a polypeptide inhibitor of Smad3 polypeptide activities. In some cases, an amino acid segment of a SH3 domain of a SNX9 polypeptide can range in length from about 12 amino acid residues to about 60 amino acid residues (e.g., from about 15 amino acid residues to about 60 amino acid residues, from about 20 amino acid residues to about 60 amino acid residues, from about 25 amino acid residues to about 60 amino acid residues, from about 12 amino acid residues to about 50 amino acid residues, from about 12 amino acid residues to about 45 amino acid residues, from about 12 amino acid residues to about 40 amino acid residues, from about 12 amino acid residues to about 35 amino acid residues, from about 15 amino acid residues to about 45 amino acid residues, from about 15 amino acid residues to about 30 amino acid residues, or from about 15 amino acid residues to about 20 amino acid residues).

TABLE 2

Amino acid segments of a SH3 domain of a SNX9 polypeptide.

| Amino acid sequence | SEQ ID NO: |
|---|---|
| IITITNPDVGGGWLEG | 6 |
| TVNEGEIITITNPDVGGGWLEGRNIKGERGL | 7 |
| MATKARVMYDFAAEPGNNELTVNEGEIITIT NPDVGGGWLEGRNIKGERGLVPTDYVEILPS | 8 |

In some cases, a polypeptide inhibitor of Smad3 polypeptide activities can have an amino acid sequence as set forth in Table 3. In some cases, a polypeptide inhibitor of Smad3 polypeptide activities described herein can range in length from about 20 amino acid residues to about 100 amino acid residues (e.g., from about 30 amino acid residues to about 100 amino acid residues, from about 40 amino acid residues to about 100 amino acid residues, from about 20 amino acid residues to about 90 amino acid residues, from about 20 amino acid residues to about 75 amino acid residues, from about 20 amino acid residues to about 50 amino acid residues, from about 30 amino acid residues to about 90 amino acid residues, from about 25 amino acid residues to about 65 amino acid residues, from about 30 amino acid residues to about 60 amino acid residues, from about 35 amino acid residues to about 55 amino acid residues, or from about 40 amino acid residues to about 50 amino acid residues).

TABLE 3

Amino acid sequences of exemplary polypeptide inhibitors of Smad3 polypeptide activities.

| Amino acid sequence | SEQ ID NO: |
|---|---|
| GYGRKKRRQRRRGSMSGYPYDVPDYAGSMTVNEGEIITITNPDVGGGWLEGRNIKGERGL | 9 |
| GYGRKKRRQRRRGSMSGYPYDVPDYAGSMMATKARVMYDFAAEPGNNELTVNEGEIITITNPDVGGGWLEGRNIKGERGLVPTDYVEILPS | 10 |
| GYGRKKRRQRRRGSMSGYPYDVPDYAGSMIITITNPDVGGGWLEG | 11 |
| GYGRKKRRQRRRGSMATKARVMYDFAAEPGNNELTVNEGEIITITNPDVGGGWLEGRNIKGERGLVPTDYVEILPS | 12 |
| GYGRKKRRQRRRGSTVNEGEIITITNPDVGGGWLEGRNIKGERGL | 13 |
| GYGRKKRRQRRRGSIITITNPDVGGGWLEG | 14 |
| RQIKIWFQNRRMKWKKMATKARVMYDFAAEPGNNELTVNEGEIITITNPDVGGGWLEGRNIKGERGLVPTDYVEILPS | 36 |
| RQIKIWFQNRRMKWKKTVNEGEIITITNPDVGGGWLEGRNIKGERGL | 15 |
| RQIKIWFQNRRMKWKKIITITNPDVGGGWLEG | 16 |
| RRRRRRRRRMATKARVMYDFAAEPGNNELTVNEGEIITITNPDVGGGWLEGRNIKGERGLVPTDYVEILPS | 17 |
| RRRRRRRRRTVNEGEIITITNPDVGGGWLEGRNIKGERGL | 18 |

TABLE 3 -continued

Amino acid sequences of exemplary polypeptide inhibitors of Smad3 polypeptide activities.

| Amino acid sequence | SEQ ID NO: |
|---|---|
| RRRRRRRRRIITITNPDVGGGWLEG | 19 |
| AGYLLGKINLKALAALAKKILMATKARVMYDFAAEPGNNELTVNEGEIIT ITNPDVGGGWLEGRNIKGERGLVPTDYVEILPS | 20 |
| AGYLLGKINLKALAALAKKILTVNEGEIITITNPDVGGGWLEGRNIKGER GL | 21 |
| AGYLLGKINLKALAALAKKILIITITNPDVGGGWLEG | 22 |
| PLIYLRLLRGQFMATKARVMYDFAAEPGNNELTVNEGEIITITNPDVGGG WLEGRNIKGERGLVPTDYVEILPS | 23 |
| PLIYLRLLRGQFTVNEGEIITITNPDVGGGWLEGRNIKGERGL | 24 |
| PLIYLRLLRGQFIITITNPDVGGGWLEG | 25 |

Single underline = junction;
double underline = HA tag amino acid sequence

A polypeptide inhibitor of Smad3 polypeptide activities can have one or more amino acid substitutions (e.g., one, two, three, four, five, six, seven, or more) relative to an amino acid sequences set forth in Tables 1-3. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, amino acid residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Further examples of conservative substitutions that can be made at any position within a polypeptide described herein are set forth in Table 4.

TABLE 4

Examples of conservative amino acid substitutions

| Original Residue | Exemplary substitutions | Preferred substitutions |
|---|---|---|
| Ala | Val, Leu, Ile | Val |
| Arg | Lys, Gln, Asn | Lys |

TABLE 4-continued

Examples of conservative amino acid substitutions

| Original Residue | Exemplary substitutions | Preferred substitutions |
|---|---|---|
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, a polypeptide provided herein can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the polypeptide using, for example, methods disclosed herein.

In some cases, a nucleic acid molecule can be designed to encode a polypeptide described herein. For example, a viral vector can be constructed to encode a polypeptide having an amino acid sequence set forth in Table 3. Nucleic acid molecules encoding a polypeptide described herein can be identified and isolated using molecular biology techniques, e.g., as described by Sambrook et al., *Molecular Cloning: A Laboratory Manual*, Cold Spring Harbor Laboratory Press, NY (1989).

Vectors containing a nucleic acid encoding a polypeptide described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors provided herein, a nucleic acid (e.g., a nucleic acid encoding a polypeptide described herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. In some cases, an expression vector such as pTAT-HA, pGEX4T2, or pSF-CMV-Neo can be used to deliver a polypeptide described herein to a mammal (e.g., a human, a rodent such as a mouse or rat, a dog, a cat, a pig, a bovine species, or a horse) to be treated. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

As described herein, a polypeptide containing a cell penetrating amino acid sequence and an amino acid segment of a SH3 domain of a SNX9 polypeptide, or a nucleic acid encoding such a polypeptide, can be used to inhibit Smad3 polypeptide activities. Examples of Smad3 polypeptide activities that can be inhibited by a polypeptide described herein include, without limitation, phosphorylated Smad3 nuclear import, soft agar colony formation, target gene/ protein expression, migration/invasion, and lung fibrosis (e.g., lung fibrosis in a murine model such as profibrotic target genes and lung function as defined by peripheral blood oxygenation). In some cases, a polypeptide containing a cell penetrating amino acid sequence and an amino acid segment of a SH3 domain of a SNX9 polypeptide can be used to treat a mammal having a disease such as carpal tunnel syndrome, lung, kidney, and/or liver fibrosis, glomerulosclerosis, cirrhosis, vascular restenosis, radiation-induced fibrosis, multiple sclerosis, traumatic brain injury, proliferative vitreoretinopathy, ocular capsule injury, or scleroderma. Examples of mammals that can be treated as described herein include, without limitation, humans, rodents (e.g., mice or rats), rabbits, simian species, ovine species, porcine species, bovine species, canine species, horses, or cats.

Any appropriate method can be used to formulate a polypeptide containing a cell penetrating amino acid sequence and an amino acid segment of a SH3 domain of a SNX9 polypeptide, or a nucleic acid encoding such a polypeptide, into a therapeutic composition. In addition, any appropriate method can be used administer such a therapeutic composition to a mammal as described herein. Dosages typically are dependent on the responsiveness of the mammal to the therapeutic composition, with the course of treatment lasting from several days to several months, or until a suitable response is achieved. Optimum dosages can vary depending on the relative potency of a therapeutic composition, and generally can be estimated based on those levels found to be effective in in vitro and/or in vivo animal models. Therapeutic compositions provided herein may be given once or more daily, weekly, monthly, or even less often, or can be administered continuously for a period of time (e.g., hours, days, or weeks).

The polypeptides, or nucleic acids, can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

This document also provides methods and materials for using RNA interference to treat a disease (e.g., a fibrotic disease) in a mammal (e.g., a human). For example, siRNA or shRNA can be designed to target SNX9 nucleic acid and trigger RNA interference against SNX9 nucleic acid expression. In some cases, a human SNX9 nucleic acid sequence can be used to design an siRNA or an shRNA that targets SNX9 nucleic acid and triggers RNA interference against SNX9 nucleic acid expression. A human SNX9 nucleic acid can be as set forth in Genbank Accession No. NM 016224 (GI No. 525313625). Examples of siRNA molecules that can be used to trigger RNA interference against human SNX9 nucleic acid expression include, without limitation, GCUGCUGAACCUGGAAAUA (SEQ ID NO:26), GGUUCCCACAGACUACGUU (SEQ ID NO:27), CCAAAGAAAGAUCUCCAUU (SEQ ID NO:28), GCACUCACAAGGGAGCAAU (SEQ ID NO:29), AACAGUCGUGCUAGUUCCUCA (SEQ ID NO:30; Soulet et al., *Mol. Biol. Cell.*, 16(4):2058-2067 (2005)), UAAGCACUUUGACUGGUUAUU (SEQ ID NO:31; Bendris et al., *Mol. Biol. Cell.*, 27(9):1409-1419 (2016)), and GGGACUUUGUAGAGAAUUU (SEQ ID NO:32; Bendris et al., *Mol. Biol. Cell.*, 27(9):1409-1419 (2016)).

Any appropriate method can be used to design an siRNA or an shRNA that targets SNX9 nucleic acid and triggers RNA interference against SNX9 nucleic acid expression. For example, software programs such as those described elsewhere (see, e.g., Naito et al., *Nucleic Acids Res.*, 32(Web Server issue):W124-W129 (2004)) can be used to design an siRNA or an shRNA that targets SNX9 nucleic acid (e.g., human SNX9 nucleic acid) and triggers RNA interference against SNX9 nucleic acid expression (e.g., human SNX9 nucleic acid expression).

Once designed, a particular siRNA or shRNA can be assessed in vitro or in vivo to confirm its ability to trigger RNA interference against SNX9 nucleic acid expression (e.g., human SNX9 nucleic acid expression). For example, a particular siRNA or shRNA can be administered to a mammal, and the level of SNX9 nucleic acid or SNX9 polypeptide expression within the mammal (or particular tissues or cells of the mammal) can be assessed before and after administration to identify those siRNA or shRNA molecules having the ability to trigger RNA interference against SNX9 nucleic acid expression. In some cases, the methods and materials described elsewhere (e.g., Soulet et al., *Mol. Biol. Cell.*, 16(4):2058-2067 (2005), or Bendris et al., *Mol. Biol. Cell.*, 27(9):1409-1419 (2016)) can be used to confirm that a particular siRNA or shRNA has the ability to trigger RNA interference against SNX9 nucleic acid expression.

Any appropriate method can be used to deliver one or more siRNA or shRNA molecules provided herein to cells or tissue within a mammal such as those described elsewhere (e.g., Kanasty et al., *Nature Materials*, 12(11):967-977 (2013) or Xu et al., *Asian Journal of Pharmaceutical Sciences*, 10(1):1-12 (2015)). For example, siRNA or shRNA having the ability to trigger RNA interference against SNX9 nucleic acid expression can be configured into lipid nanoparticles such as those described elsewhere (e.g., U.S. Patent Application Publication No. 2011/0224447) to deliver the siRNA or shRNA to cells within a mammal (e.g., a human). In some cases, one or more siRNA and/or shRNA molecules having the ability to trigger RNA interference against SNX9 nucleic acid expression provided herein can be delivered to liver cells within a mammal to treat, for example, liver fibrosis. For example, delivery vehicles containing N-acetyl-d-galactosamine such as those described elsewhere (e.g., Dhande et al., *Biomacromolecules*, 17(3): 830-840 (2016)) can be used to deliver one or more siRNA and/or shRNA molecules having the ability to trigger RNA interference against SNX9 nucleic acid expression to cells (e.g., liver cells). In some cases, siRNA conjugated with α-tochopherol using techniques such as those described elsewhere (e.g., Murakami et al., *Scientific Report*, 5:17035 (2015)) can be used to deliver one or more siRNA and/or shRNA molecules having the ability to trigger RNA interference against SNX9 nucleic acid expression to cells (e.g., liver cells). In some cases, cyclodextrin compositions such as those described elsewhere (e.g., Arima et al., *Curr. Top. Med. Chem.*, 14(4):465-77 (2014)) can be used to deliver one or more siRNA and/or shRNA molecules having the ability to trigger RNA interference against SNX9 nucleic acid expression to cells. In some cases, a biodegradable polymeric matrix such as those described elsewhere (e.g., Ramot et al., *Toxicol Pathol.*, May 4 (2016) or Golan et al., *Oncotarget.*, 6(27):24560-70 (2015)) can be used to deliver one or more siRNA and/or shRNA molecules having the ability to trigger RNA interference against SNX9 nucleic acid expression to cells. In some cases, aerosol formulations of siRNA such as those described elsewhere (e.g., Lam et al., *Adv. Drug. Deliv. Rev.*, 64(1):1-15 (2012)) can be used for pulmonary delivery of one or more siRNA and/or shRNA molecules having the ability to trigger RNA interference against SNX9 nucleic acid expression to cells.

As described herein, a composition can be formulated to contain one or more siRNA and/or shRNA molecules having the ability to trigger RNA interference against SNX9 nucleic acid expression (e.g., a composition can be formulated to contain one or more siRNA and/or shRNA molecules having the ability to trigger RNA interference against SNX9 nucleic acid expression in combination with a deliver vehicle such as a lipid nanoparticle, N-acetyl-d-galactosamine, cyclodextrin, and/or biodegradable polymeric matrix such as those described above). Such a composition containing one or more siRNA and/or shRNA molecules having the ability to trigger RNA interference against SNX9 nucleic acid expression can be administered to a mammal to treat a disease. Examples of diseases that can be treated with a composition containing one or more siRNA and/or shRNA molecules having the ability to trigger RNA interference against SNX9 nucleic acid expression include, without limitation, carpal tunnel syndrome, lung, kidney, and/or liver fibrosis, glomerulosclerosis, cirrhosis, vascular restenosis, radiation-induced fibrosis, multiple sclerosis, traumatic brain injury, proliferative vitreoretinopathy, ocular capsule injury, and scleroderma. In some cases, a composition containing one or more siRNA and/or shRNA molecules having the ability to trigger RNA interference against SNX9 nucleic acid expression can be administered to a mammal to treat a fibrotic disease (e.g., lung, kidney, and/or liver fibrosis).

In some cases, a nucleic acid molecule can be designed to express an siRNA and/or shRNA molecule having the ability to trigger RNA interference against SNX9 nucleic acid expression. For example, a viral vector can be constructed to encode an siRNA and/or shRNA molecule having the ability to trigger RNA interference against SNX9 nucleic acid expression.

In the expression vectors provided herein, a nucleic acid (e.g., a nucleic acid encoding an siRNA and/or shRNA molecule having the ability to trigger RNA interference against SNX9 nucleic acid expression) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II).

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. In some cases, an expression vector such as pTAT-HA, pGEX4T2, or pSF-CMV-Neo can be used to deliver an siRNA and/or shRNA molecule described herein to a mammal (e.g., a human, a rodent such as a mouse or rat, a dog, a cat, a pig, a bovine species, or a horse) to be treated. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.).

As described herein, an siRNA and/or shRNA molecule described herein, or a nucleic acid encoding such an siRNA and/or shRNA molecule described herein, can be used to inhibit Smad3 polypeptide activities. Examples of Smad3 polypeptide activities that can be inhibited by an siRNA and/or shRNA molecule having the ability to trigger RNA interference against SNX9 nucleic acid expression include, without limitation, phosphorylated Smad3 nuclear import, soft agar colony formation, target gene/protein expression, migration/invasion, and lung fibrosis (e.g., lung fibrosis in a murine model such as profibrotic target genes and lung function as defined by peripheral blood oxygenation). In some cases, an siRNA and/or shRNA molecule having the ability to trigger RNA interference against SNX9 nucleic acid expression can be used to treat a mammal having a disease such as carpal tunnel syndrome, lung, kidney, and/or liver fibrosis, glomerulosclerosis, cirrhosis, vascular restenosis, radiation-induced fibrosis, multiple sclerosis, traumatic brain injury, proliferative vitreoretinopathy, ocular capsule injury, or scleroderma. Examples of mammals that can be treated using an siRNA and/or shRNA molecule having the ability to trigger RNA interference against SNX9 nucleic acid expression as described herein include, without limitation, humans, rodents (e.g., mice or rats), rabbits, simian species, ovine species, porcine species, bovine species, canine species, horses, or cats.

Any appropriate method can be used to formulate an siRNA and/or shRNA molecule having the ability to trigger RNA interference against SNX9 nucleic acid expression, or a nucleic acid encoding such an siRNA and/or shRNA molecule, into a therapeutic composition. In addition, any appropriate method can be used administer such a therapeutic composition to a mammal as described herein. Dosages typically are dependent on the responsiveness of the mammal to the therapeutic composition, with the course of treatment lasting from several days to several months, or until a suitable response is achieved. Optimum dosages can vary depending on the relative potency of a therapeutic composition, and generally can be estimated based on those levels found to be effective in in vitro and/or in vivo animal models. Therapeutic compositions provided herein may be given once or more daily, weekly, monthly, or even less often, or can be administered continuously for a period of time (e.g., hours, days, or weeks).

An siRNA and/or shRNA molecule described herein, or nucleic acid encoding an siRNA and/or shRNA molecule described herein, can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

The invention will be further described in the following examples, which do not limit the scope of the invention described in the claims.

EXAMPLES

Example 1—Inhibition of Profibrotic Smad3 Action by Cell Penetrating Peptides that Block Smad3 Nuclear Import Cell Culture AKR-2B cells were grown in DMEM supplemented with 10% fetal bovine serum (FBS). Prior to use, $2.5 \times 10^5$ cells were seeded on 6 well plates and cultured in 10% FBS/DMEM. The next day, the medium was replaced with 0.5% FBS/DMEM, and cells were transduced for 90 minutes with the indicated TAT-containing polypeptide. After transduction, cells were incubated with or without TGFβ (5 ng/mL) for the indicated times in 0.5% FBS/DMEM.

Generation of TAT-SNX9(SH3) Fusion Polypeptides

TAT-SNX9(SH3) fusion polypeptides were prepared from BL21(DE3)pLysS *E. coli* (OD600 of 0.4) using techniques similar to those described elsewhere (Wilkes et al., Mol. Biol. Cell., 26(21):3879-91 (2015)). Briefly, following addition of isopropyl β-d-thiogalactopyranoside to a final concentration of 0.5 mM and 4 hours induction at 37° C., lysates were prepared, and the precleared supernatant poured into a TALON Metal Affinity Resin column (Clontech, Mountain View, Calif.). Polypeptides were eluted (50 mM sodium phosphate, 300 NaCl, and 150 mM imidazole, pH7.4) and dialyzed against PBS using a Slide-A Lyzer Mini Dialysis unit (Thermo Scientific, Rockford, Ill.).

Soft Agar Assay

Soft agar assays were performed as described elsewhere (Rahimi et al., Cancer Res., 69(1):84-93 (2009)). Briefly, $1 \times 10^4$ cells in 10% FBS/DMEM were seeded in a 6 well plate in the presence or absence of 10 ng/mL TGFβ (R&D Systems, Minneapolis, Minn.) and the indicated TAT-SNX9 (SH3) fusion polypeptides. Following 7 days growth at 37° C., the number of colonies>100 μm in diameter were counted using an Optronix Gelcount™ (Oxford Optronics, Milton, Abingdon, UK). The results were representative of three separate experiments, each done in triplicate.

Luciferase Reporter Assays

For luciferase assays, $2 \times 10^5$ cells were plated in six well plates containing 10% FBS/DMEM. The next day, cells were transfected with 2 (3TP, BRE, SRE, and MMP1) or 1.5 (ARE; plus 1.5 μg FAST1) μg of the indicated luciferase constructs together with 0.5 μg cytomegalovirus (CMV)-β-galactosidase with TransIT-2020 reagent (Minis Bio, Madison, Wis., USA). Following 24 hour incubation at 37° C., the medium was changed to 0.5% FBS/DMEM, and the cultures were treated with the indicated TAT-SNX9(SH3) fusion polypeptides for 90 minutes. After transduction, cultures were incubated in the presence or absence of 5 ng/mL TGFβ for 12 hours in 0.5% FBS/DMEM. Cells were harvested in 200 μL of reporter lysis buffer (Promega, Madison, Wis.), and luciferase activity was determined in a Berthold Lumat 9507 luminometer after normalization for transfection efficiency with β-galactosidase.

Immunofluorescent Microscopy $2 \times 10^4$ cells were plated onto coverslips in 10% FBS/DMEM and incubated overnight at 37° C. Cultures were placed in 0.5% FBS/DMEM and transduced with the indicated TAT-SNX9(SH3) fusion polypeptides for 90 minutes. After transduction and addition of TGFβ (5 ng/mL) for 1 hour, cells were processed as described elsewhere (Wilkes et al., *Mol. Biol. Cell.*, 26(21):3879-91 (2015)). Smad3 was detected using AF488 secondary antibodies (green), while the HA tag of the TAT-SNX9(SH3) fusion polypeptides was visualized with AF-594 (red) secondary antibodies, both from Invitrogen (Carlsbad, Calif.). Fluorescence images were collected on a LSM510 confocal microscope (Carl Zeiss Microimage Inc. Thornwood, N.Y.). Both AF488 and AF594 were secondary antibodies. The primary antibodies were those to Smad3 and HA, respectively.

Quantitative Reverse Transcription (RT)-PCR Analysis

Following TGFβ stimulation, total RNA was isolated using Rneasy plus Mini kit (QIAGEN, Valencia, Calif.), and 1 μg reverse transcribed with the SuperScript® III Reverse Transcriptase system (Invitrogen, CA). Complementary DNAs were subjected to qPCR with platinum SYBR green qPCR superMix-UDG (Invitrogen, CA) or TaqMan gene expression analysis (Thermo Scientific, Rockford, Ill.), and sample induction was normalized to Histone H3.

Western Blotting

Cells were lysed for 30 minutes on ice in RIPA buffer (50 mM Tris, pH 7.4, 1% Triton X100, 0.25% Sodium deoxycholate, 150 mM NaCl, 1 mM EDTA, pH 8, and 10 mM NaF) containing protease inhibitor cocktail tablets (Roche, Indianapolis). Insoluble material was removed by centrifugation at 18,000×g for 10 minutes, and 10-25 µg of protein was separated by 10% SDS-PAGE. Phospho-Smad2 and -Smad3 specific antibodies were generated, while anti-GAPDH and anti-His tag antibodies were obtained from EMD Millipore (Darmstadt, Germany). Anti-PAI-1, -CTGF, and -histone deacetylase 1 (HDAC1) antibodies were obtained from Santa Cruz Biotechnology (Santa Cruz, Calif.) and Cell Signaling (Danvers, Mass.).

GST and his Pull-Down

Fusion polypeptides containing GST- or His-tags were purified using Glutathione Superflow or TALON Metal Affinity Resin, respectfully, following the manufacturer's instructions (Clontech, Mountain View, Calif.). To assess SNX9 binding to GST or His constructs, cells were incubated in the presence or absence of 5 ng/mL TGFβ for 45 minutes. Following RIPA buffer lysis, 500 µg of protein was precleared with GST Resin or TALON Metal Affinity Resin for 2 hours at 4° C. Precleared cell lysates were then treated with 5 µg purified GST- or His-fusion proteins and incubated overnight at 4° C. with gentle shaking. Following addition of GST or TALON Metal Affinity Resin and 2 hours of incubation, the pelleted (3,000×g; 10 minutes) resin was washed several times with PBS, and the remaining proteins were eluted using 1× Laemmli sample buffer. Western blotting was performed as described above.

Isolation of Nuclear Fractions

Nuclear extracts were prepared using NE-PER Nuclear and Cytoplasmic Extraction Kits for Cultured Cells (Thermo Scientific, Rockford, Ill.) with the addition of protease inhibitor (Roche, Indianapolis, Ind.) to the lysis buffers. Following removal of the cytoplasmic extract, the nuclear pellet was washed three times in PBS containing protease inhibitor before nuclear lysis and Western analysis.

Animal Models of Pulmonary Fibrosis

Female 18-20 g C57 black mice (Charles River Laboratories) were administered bleomycin (BLM; 0.075 U diluted in 50 µL 0.9% normal saline) or 50 µL 0.9% normal saline alone by tracheal instillation using an intratracheal aerosolized (Penn-century, Wyndmoor, Pa.) as described elsewhere (Andrianifahanana et al., $FASEB$ $J.$, 27(11):4444-54 (2013)). At this time, animals were shaved around the collar region to allow monitoring of dissolved oxygen levels (every 3rd day) on room air using a MouseOX collar clip monitoring system (Starr Life Science Corp. Oakmont, Pa.). TAT-SNX9(SH3) fusion polypeptides were solubilized with DMSO and prepared by thoroughly blending with Methocel (Sigma, Louis, Mo.) at a ratio of 1:7. Mice were treated daily by intraperitoneal injection (100 µL) of a TAT-SNX9(SH3) fusion polypeptide or an equal volume of methocel/saline beginning on day 14. On day 28, mice were euthanized, lungs were dissected, and samples were prepared for immunohistochemistry and other analyses as described elsewhere (Andrianifahanana et al., $FASEB$ $J.$, 27(11):4444-54 (2013); Daniels et al., $J.$ $Clin.$ $Invest.$, 114:1308-16 (2004); and Wang et al., $FASEB$ $J.$, 19:1-11 (2005)).

Hydroxyproline Assay

The Hydroxyproline Assay Kit from Sigma (St. Louis, Mo.) was used to assess total lung collagen levels. Briefly, following sacrifice lung tissue was washed in PBS, and 30 mg homogenized in 300 µL water. One hundred µL samples were hydrolyzed in 12 M HCl, and duplicate 50 µL samples were analyzed according to the manufacturer's recommendations.

Results

A TAT-Containing Sorting Nexin 9 Polypeptide Specifically Blocks pSmad3 Nuclear Import and Profibrotic TGFβ Signaling As described elsewhere, SNX9 has an obligate role in mediating profibrotic TGFβ signaling dependent upon phosphorylated (p) Smad3 (Wilkes et al., $Mol.$ $Biol.$ $Cell.$, 26(21):3879-91 (2015)). In order to investigate whether pSmad3 bound to a defined region(s) in SNX9, GST fusion constructs encoding either the amino (i.e., SH3 and low complexity (LC) domains) or carboxyl (i.e., Phox and BAR domains) half of SNX9 were generated, and pull down assays for pSmad3 were performed (FIG. 1A depicts SNX9 domain structure). While elements within the Phox and BAR domains were unable to bind pSmad3, equivalent pSmad3 binding was observed with GST full length (FL) SNX9 and the amino terminal peptide. To define this interaction further, two overlapping amino terminal fragments were generated. As shown in FIG. 1A, while equivalent pSmad3 binding was observed with constructs expressing FL SNX9 or the first 74 amino acids encoding the SH3 domain, the LC domain exhibited only minimal binding. Of note, no pSmad2 association was observed for any of the constructs, consistent with the results described elsewhere (Wilkes et al., $Mol.$ $Biol.$ $Cell.$, 26(21):3879-91 (2015)).

Figure 1B:
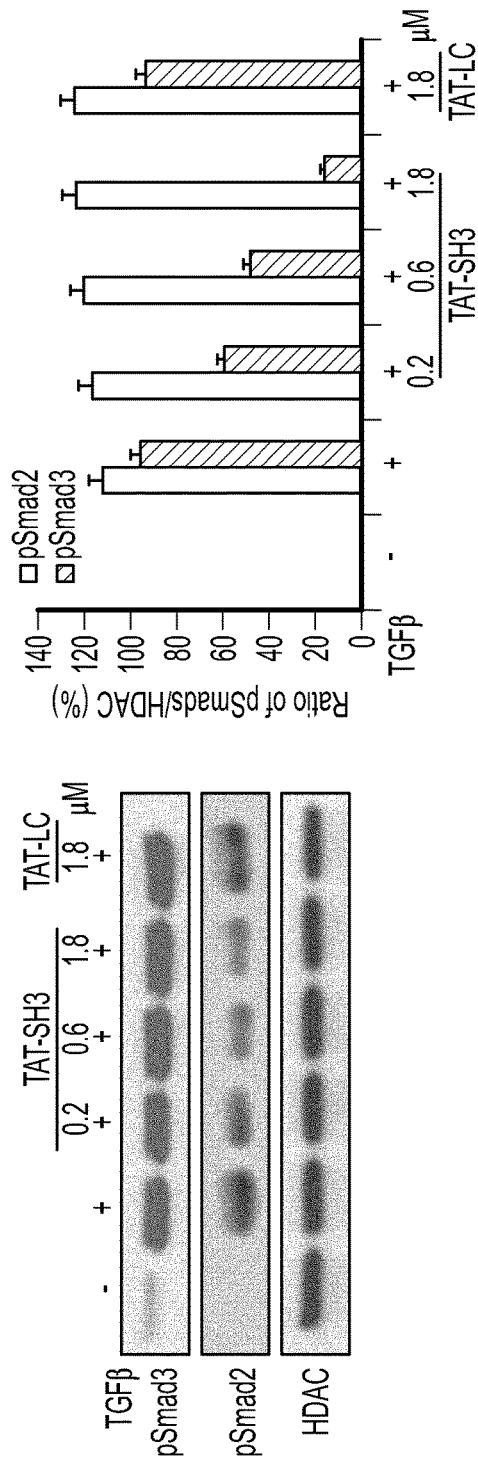
Figure 1C:
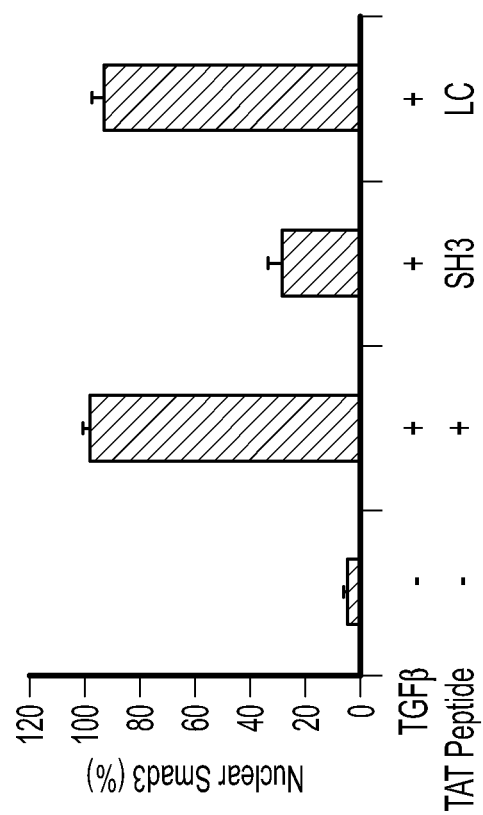
Figure 1C:
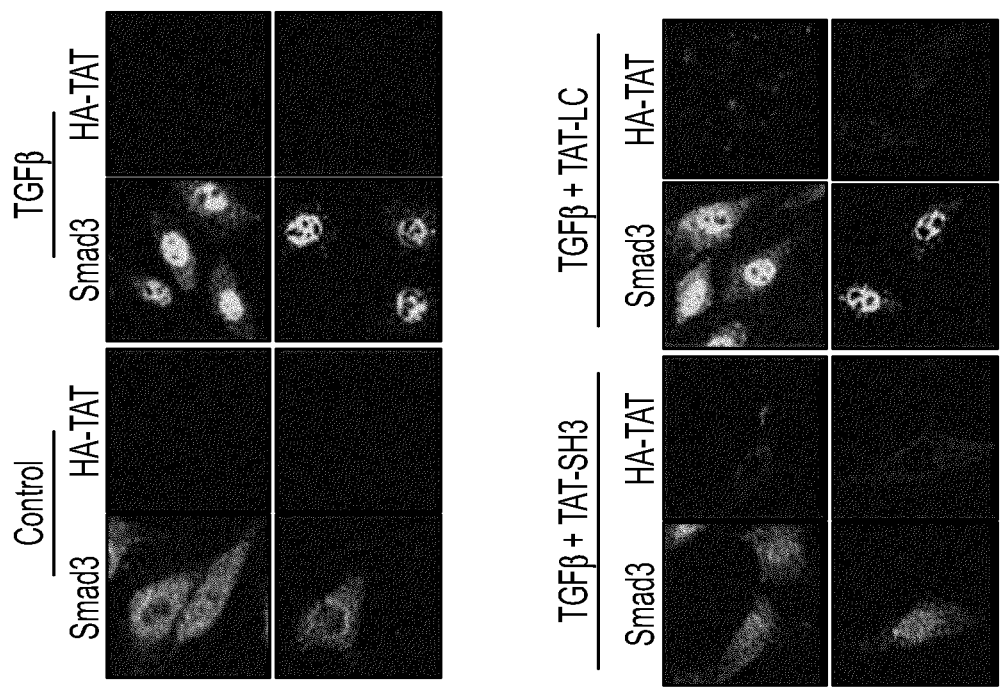

As also described elsewhere, SNX9 was found to be required for the nuclear import of pSmad3, but not pSmad2 (Wilkes et al., $Mol.$ $Biol.$ $Cell.$, 26(21):3879-91 (2015)). Since the SNX9 SH3 domain was capable of similarly binding pSmad3 as the FL protein (FIG. 1A), the following was performed to determine whether this was sufficient to inhibit pSmad3 nuclear uptake. Constructs were prepared expressing either the SNX9 SH3 or LC domains fused to a cell penetrating TAT polypeptide from HIV (Becker-Hapak et al., $Methods$, 24(3):247-56 (2001); and Rizzuti et al., $Drug$ $Discov.$ $Today$, 20(1):76-85 (2015)). Subsequent to TAT polypeptide transduction, cultures were treated with TGFβ, and nuclear accumulation of pSmad2 or pSmad3 was determined. As shown in FIG. 2B, while a TAT-SNX9(SH3) fusion polypeptide containing the full length SH3 domain (amino acids 1 to 62; designated TAT-SH3 herein) inhibited nuclear import of pSmad3 in a dose-dependent manner, it had no effect on pSmad2. Furthermore, consistent with the inability of the LC domain to bind R-Smads (FIG. 1A), it was similarly ineffective in modulating nuclear translocation (FIG. 1B). These biochemical findings were confirmed using immunofluorescence (FIG. 1C).

While the results of FIG. 1 demonstrate that a TAT-SNX9 (SH3) fusion polypeptide containing a full length SH3 domain can be capable of inhibiting the nuclear accumulation of pSmad3 following TGFβ addition, these results did not assess the functional impact of this response. As such, to investigate whether this loss was sufficient to inhibit Smad3-mediated responses, the studies shown in FIG. 2 were performed. AKR-2B cells were transfected with luciferase constructs responsive to either Smad3, Smad2, or bone morphogenetic proteins (BMPs), and the impact of inhibiting pSmad3 nuclear import by TAT-SH3 determined. While Smad3-dependent luciferase activity was inhibited about 70%, no discernible effect on either Smad2 or Smad1/5/8 (i.e., BMP) signaling was observed (FIG. 2A). These luciferase results were extended both transcriptionally as well as biologically in FIGS. 2B and 2C, respectively. While Smad3 targets and TGFβ-stimulated anchorage-independent growth in soft agar (AIG) were inhibited by transduction with TAT-SH3, induction of the Smad2 regulated MMP-2 gene was unaffected, and the negative control TAT-LC polypeptide was inert for all responses.

Figure 3D:
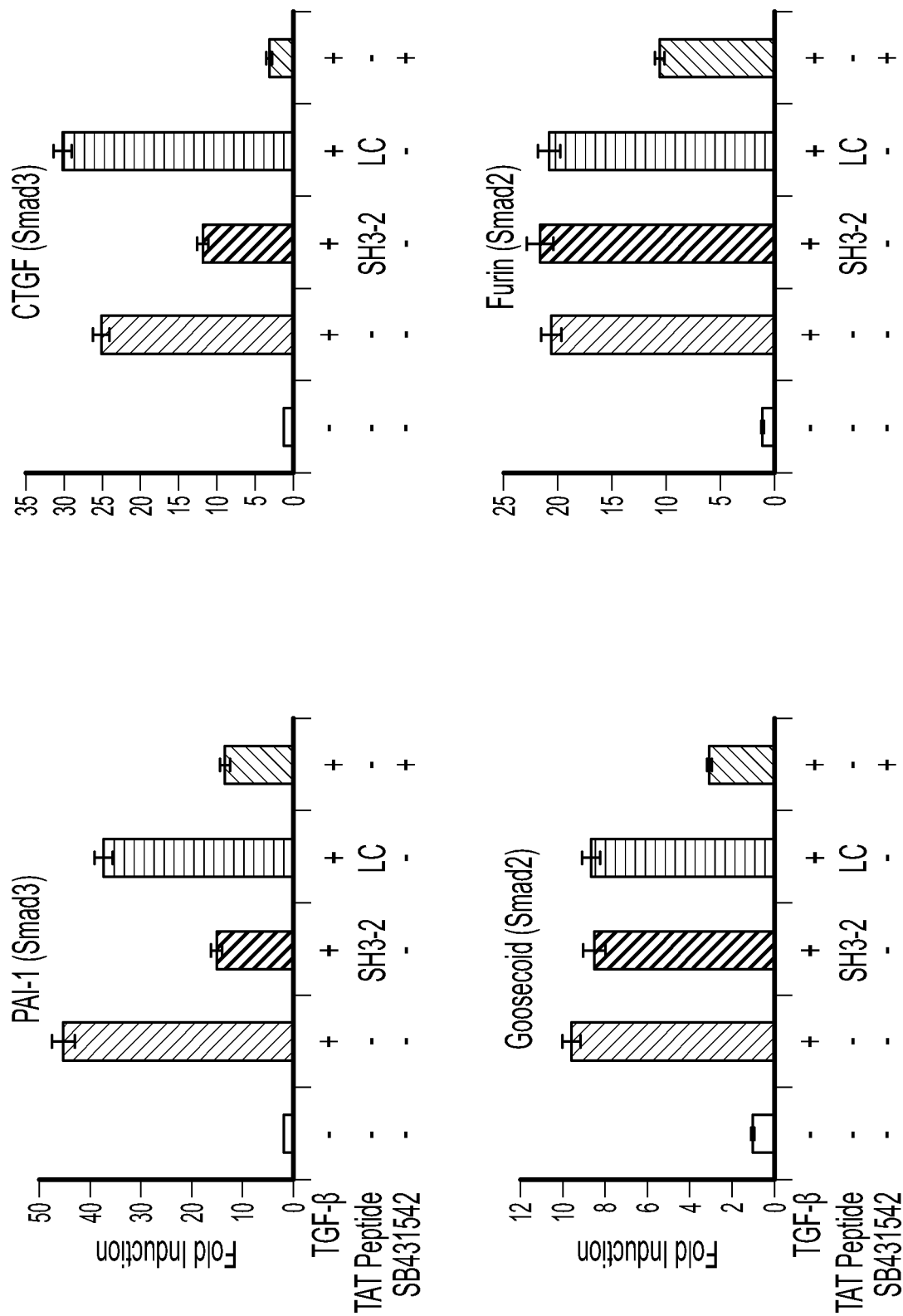
Figure 3E:
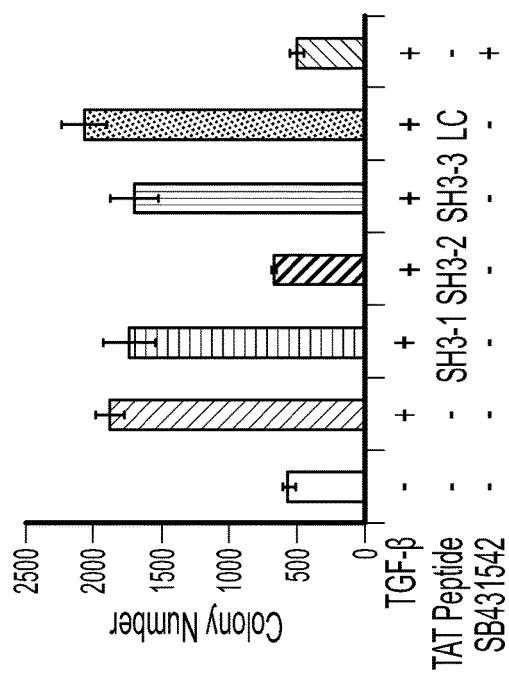

As shown in FIGS. 1-2, the expression of the SH3 domain from SNX9 can function in trans as a specific inhibitor of Smad3-regulated responses. The following was performed to define the functional motif(s) in the SH3 polypeptide regulating Smad3 signaling and to generate and test, both in vitro and in vivo, a mutant SH3 polypeptide unable to bind pSmad3. To address the first of these, three overlapping 25-31 mer TAT-SNX9(SH3) fusion polypeptides were constructed and tested for their ability to bind pSmad3 in cell lysates prepared from TGFβ treated cultures. As shown in FIGS. 3A-C, TAT-SH3-2 (a TAT-SNX9(SH3) fusion polypeptide having SNX9 amino acids 21-51) bound pSmad3 to a similar degree as a TAT-SNX9(SH3) fusion polypeptide having the full length SH3 domain (TAT-SH3) and specifically prevented pSmad3 nuclear import. Moreover, TAT-SH3-2 not only prevented Smad3-dependent transcriptional responses and AIG, but the inhibition was analogous to that observed with the TβRI kinase inhibitor SB431542 (FIGS. 3D and 3E).

Figure 4A:
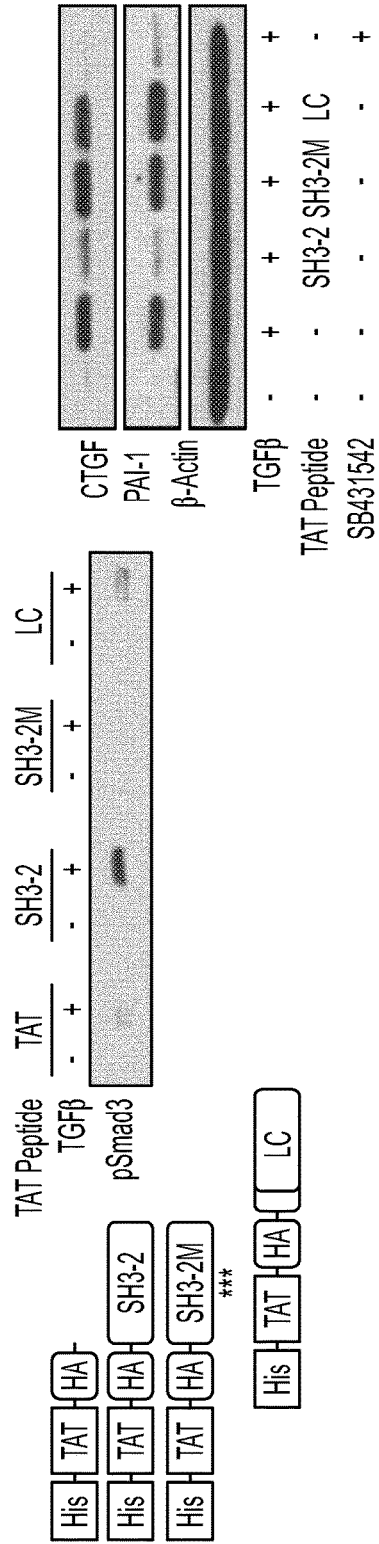
FIGS. 4A-4E. A point mutant of TAT-SH3-2 abolishes the inhibitory action on Smad3 responses. (A) Schematic depicting TAT-SNX9(SH3) fusion polypeptide constructs (Left). * in SH3-2M (mutant) reflects G to V mutations at amino acids 36-38. His pull down of pSmad3 bound to TAT-SNX9(SH3) fusion polypeptides was performed as in FIG. 3A (Middle). AKR-2B cells were transduced for 90 minutes with 1.5 µM of TAT-SH3-2, TAT-SH3-2M, or TAT-LC. Western analysis was performed for the indicated proteins following 24 hour treatment in the absence (−) or presence (+) of TGFβ (5 ng/mL) or SB431542 (10 µM) (Right). (B) qPCR of Smad3 (CTGF and Smad7) and Smad2 (Goosecoid and MixL) responsive genes as in FIG. 3D. Data reflect mean+/−sd from three experiments. (C) Scratch assays were performed on AKR-2B cells following transductions with the indicated TAT-SNX9(SH3) fusion polypeptides and are representative of three separate experiments. Red bands indicate the leading edge following 24 hours in the absence (Control) or presence of 5 ng/mL TGFβ. (D) Soft agar colony formation as in FIG. 3E. Data reflects the mean+/−sd of triplicate wells from three experiments. (E) AKR-2B cells were transiently transfected with a BMP (BRE), EGF (SRE), or PDGF (MMP-1) reporter construct and luciferase activity determined following 12 hour incubation in the absence (−) or presence (+) of the indicated ligand (10 ng/mL BMP4, EGF, or PDGF), inhibitor (10 µM Dorsomophin; 3 µM Lapatinib; 2 µM CP868) or TAT-SNX9(SH3) fusion polypeptide (1.5 µM). Data represent the mean+/−SEM of n=3 for BRE and n=2 for SRE and MMP-1.
Figure 4B:
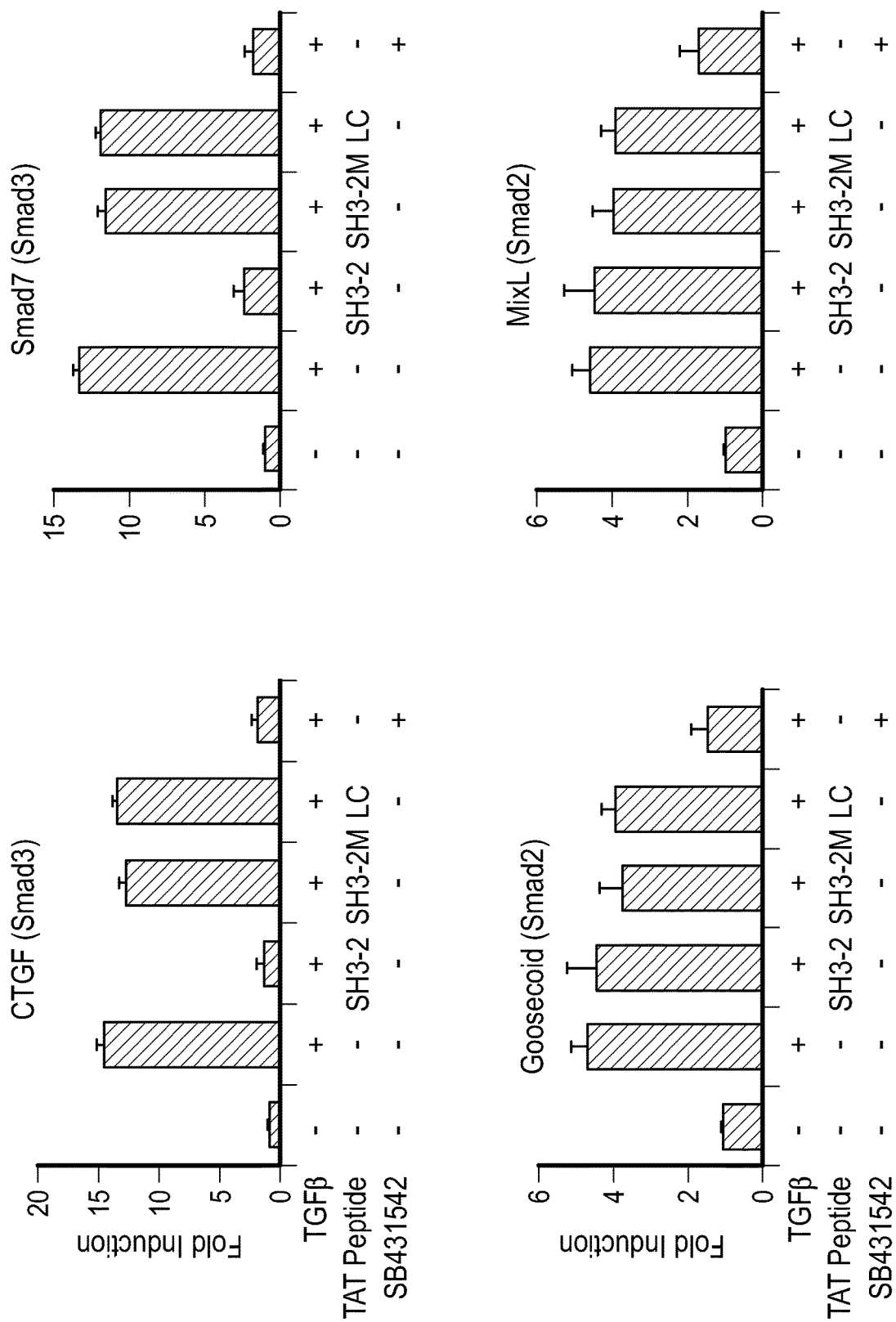
Figure 4C:
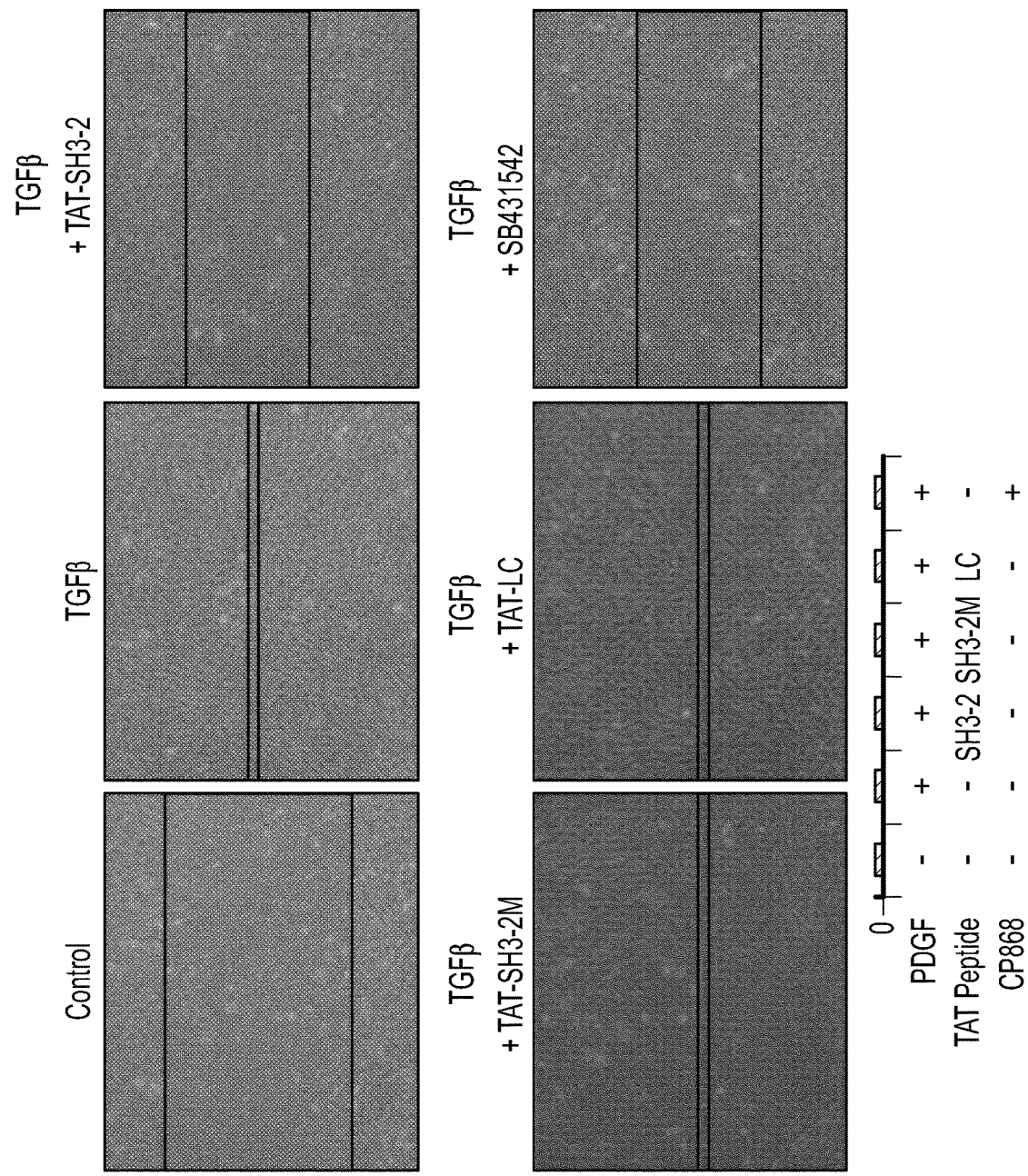
Figures 4D, 4E:
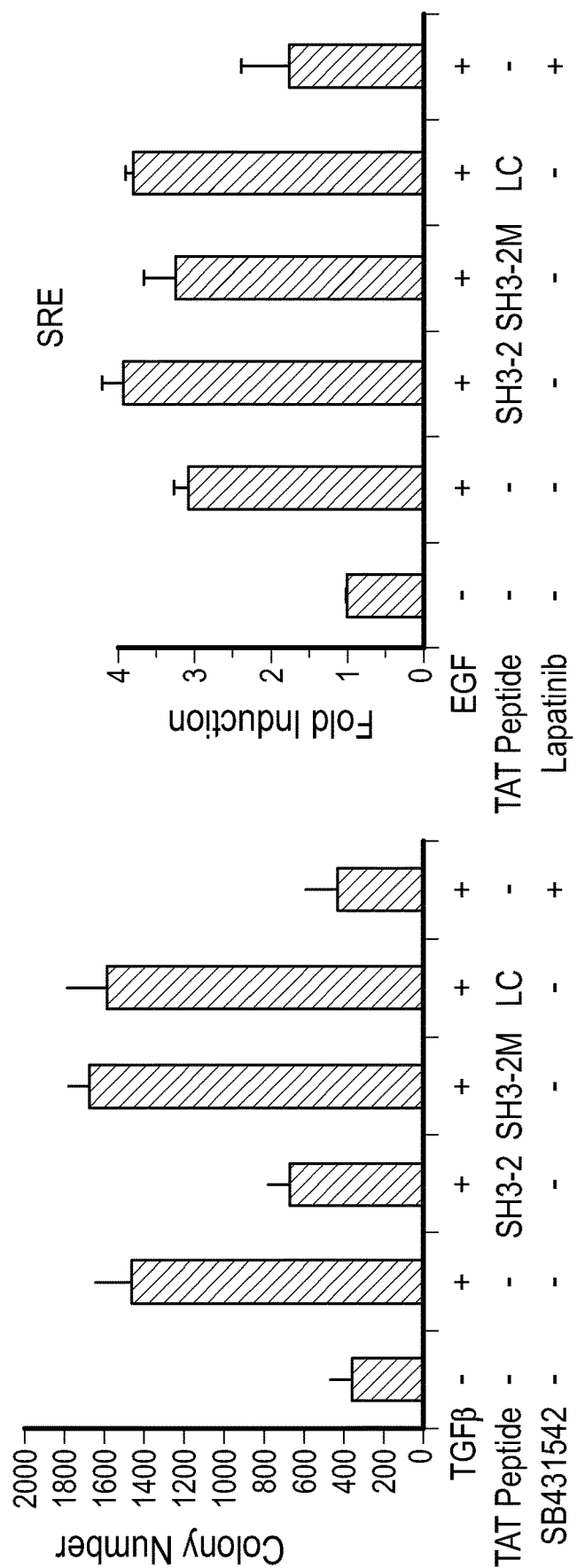

To define the element further, three additional overlapping 15 or 16 mer TAT-SNX9(SH3) fusion polypeptides were generated and assessed whether they could inhibit pSmad3 nuclear translocation. While activity similar to that obtained with SB431542 was observed with a TAT-containing polypeptide encoding amino acids 27-42 of SNX9, additional studies revealed that the 16 mer did not provide as consistent responses as the 31 mer designated TAT-SH3-2. It did, however, suggest that point mutations in a highly conserved glycine rich region, which was previously shown to mediate protein/protein interactions (Harrison et al., *J. Biol. Chem.*, 285(26):20213-23 (2010); Jang and Greenwood, *Biochem. Biophys. Res. Commun.*, 380(3):484-8 (2009); and Shaw et al., *J. Biochem.*, 147(6):885-93 (2010)), might similarly be effective in blocking the inhibitory actions of TAT-SH3-2. This was directly tested in FIG. 4. While TAT-SH3-2 bound pSmad3 and prevented TGFβ induction of Smad3 targets such as CTGF, PAI-1, and Smad7 to a similar degree as inhibition of TβRI (FIG. 3), point mutations in amino acids 36-38 (TAT-SH3-2M) abolished the inhibitory effect (FIGS. 4A and 4B). Neither polypeptide impacted the induction of Smad2 targets (FIG. 4B). Furthermore, identical results were observed when Smad3-regulated biological responses were examined in the presence of TAT-SH3-2 (inhibitory) or TAT-SH3-2M (not inhibitory) (FIGS. 4C and 4D). Last, to further confirm the specific action of TAT-SH3-2 on Smad3 action, FIG. 4E shows that the luciferase activity stimulated by BMP4, EGF, or PDGF responsive reporters is unaffected by any of the TAT-SNX9(SH3) fusion polypeptides.

Figure 5A:
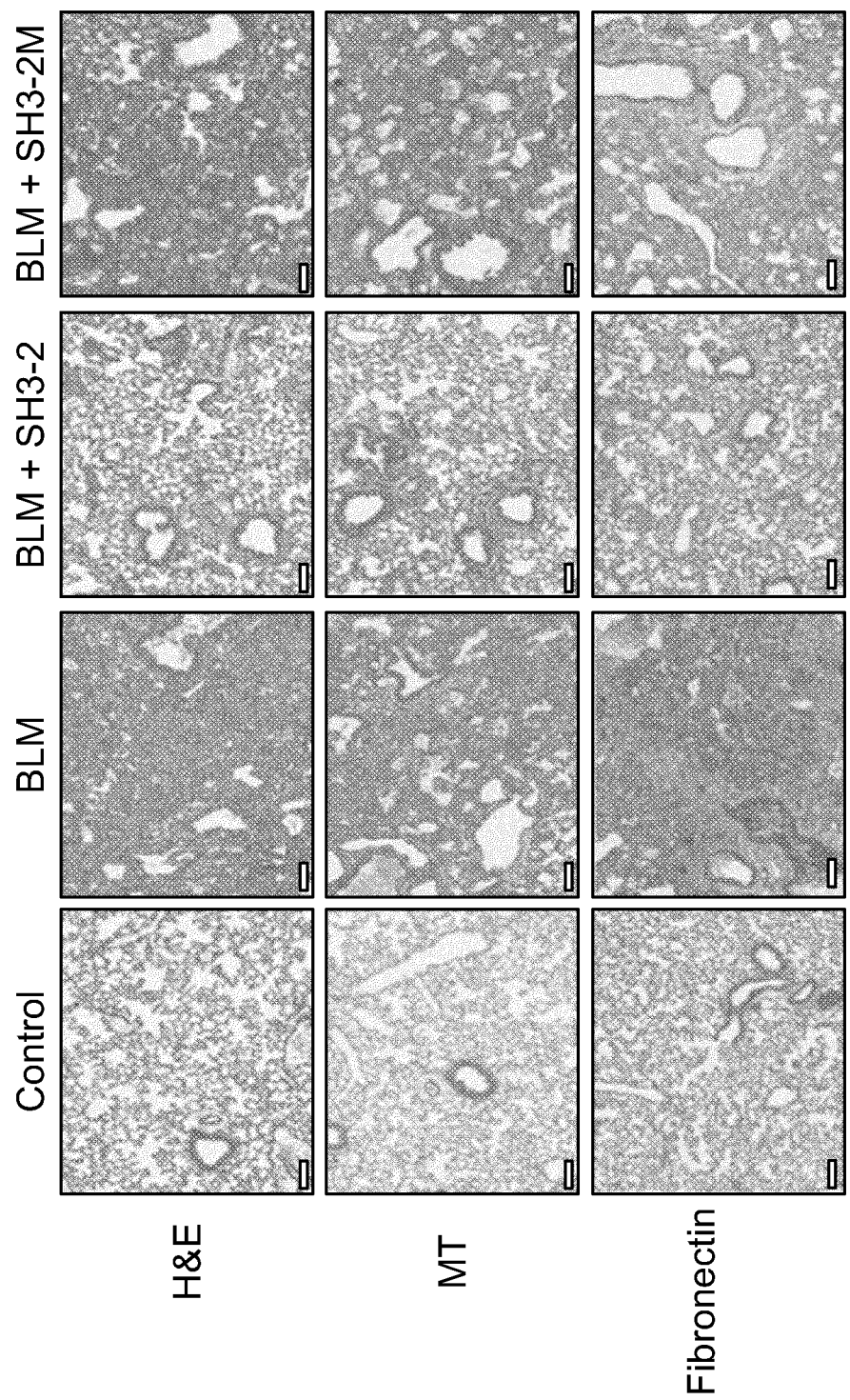
Figure 5D:
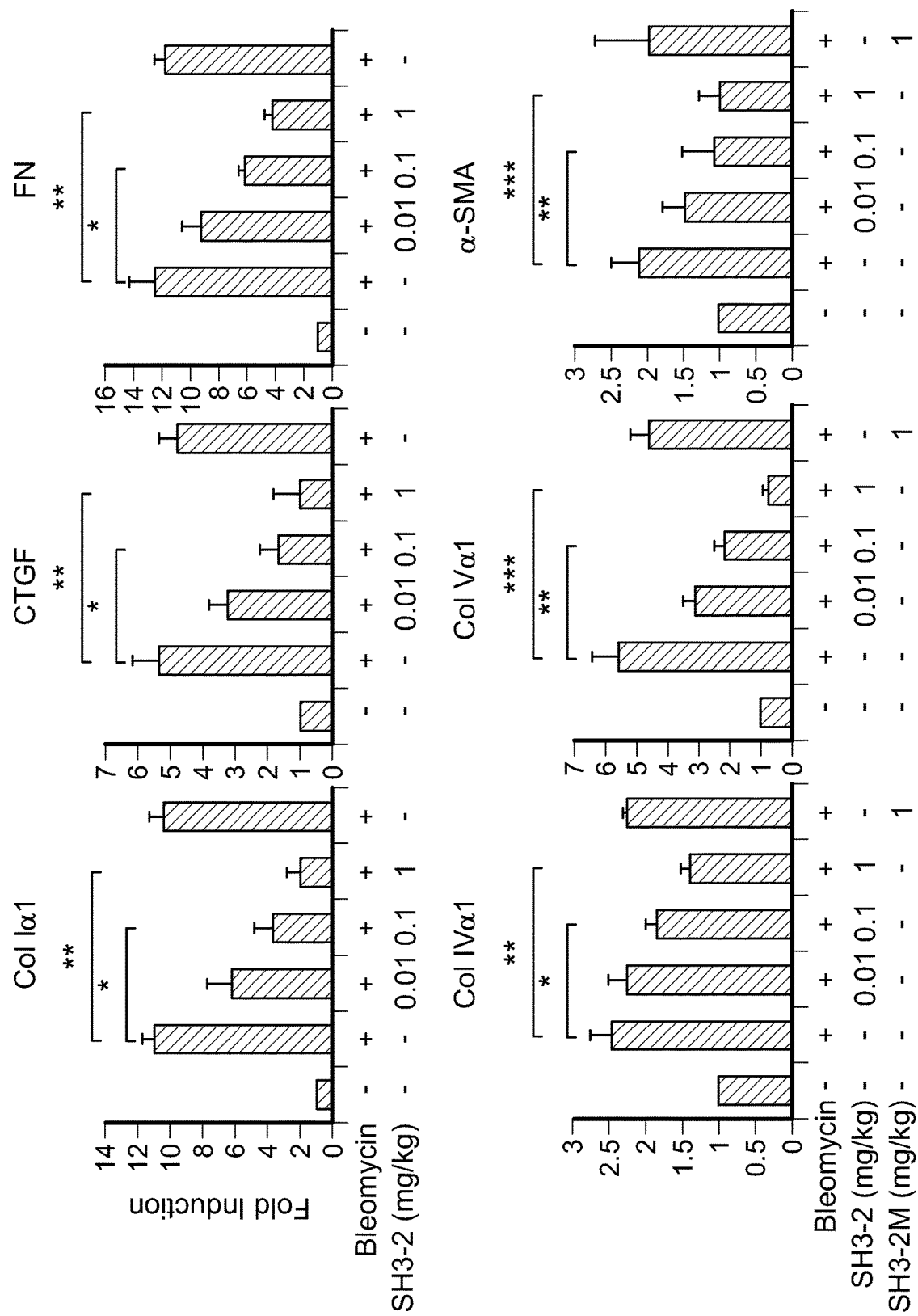

Cell Penetrating Peptides that Block pSmad3 Action are Effective in a Treatment Model of Pulmonary Fibrosis As demonstrated herein, a cell penetrating polypeptide encoding a defined region of SNX9 that prevents pSmad3 nuclear import can act in trans to inhibit TGFβ-stimulated biochemical, translational, transcriptional, and biological actions dependent upon pSmad3. Furthermore, the degree of inhibition is analogous to that obtained with a small molecule inhibitor of the TβRI kinase and Smad2-, Smad1/5/8-, EGF-, and/or PDGF-stimulated responses are unaffected. Profibrotic actions of TGFβ are primarily mediated via Smad3 (Hoot et al., *J. Clin. Invest.*, 118(8):2722-32 (2008); and Meng et al., *J. Am. Soc. Nephrol.*, 21(9):1477-87 (2010)). A treatment model of bleomycin (BLM)-induced lung fibrosis was used to test, in vivo, the efficacy of intraperitoneal administration of TAT-SH3-2 (or TAT-SH3-2M) commencing 14 days following initial BLM insult. As shown in FIGS. 5A and 5C, while TAT-SH3-2 improved lung histology, reduced interstitial fibronectin to essentially basal levels, and showed a dose-dependent diminization in total collagen production induced by bleomycin, the TAT-SH3-2M peptide unable to bind pSmad3 (FIG. 4A) was ineffective. Consistent with the immunohistochemistry, qPCR analysis of similarly treated murine lung tissue showed that TAT-SH3-2 polypeptides, but not TAT-SH3-2M, significantly reduced the BLM induction of profibrotic genes including collagen 1, connective tissue growth factor, and fibronectin (FIGS. 5B and 5D).

Figure 6A:
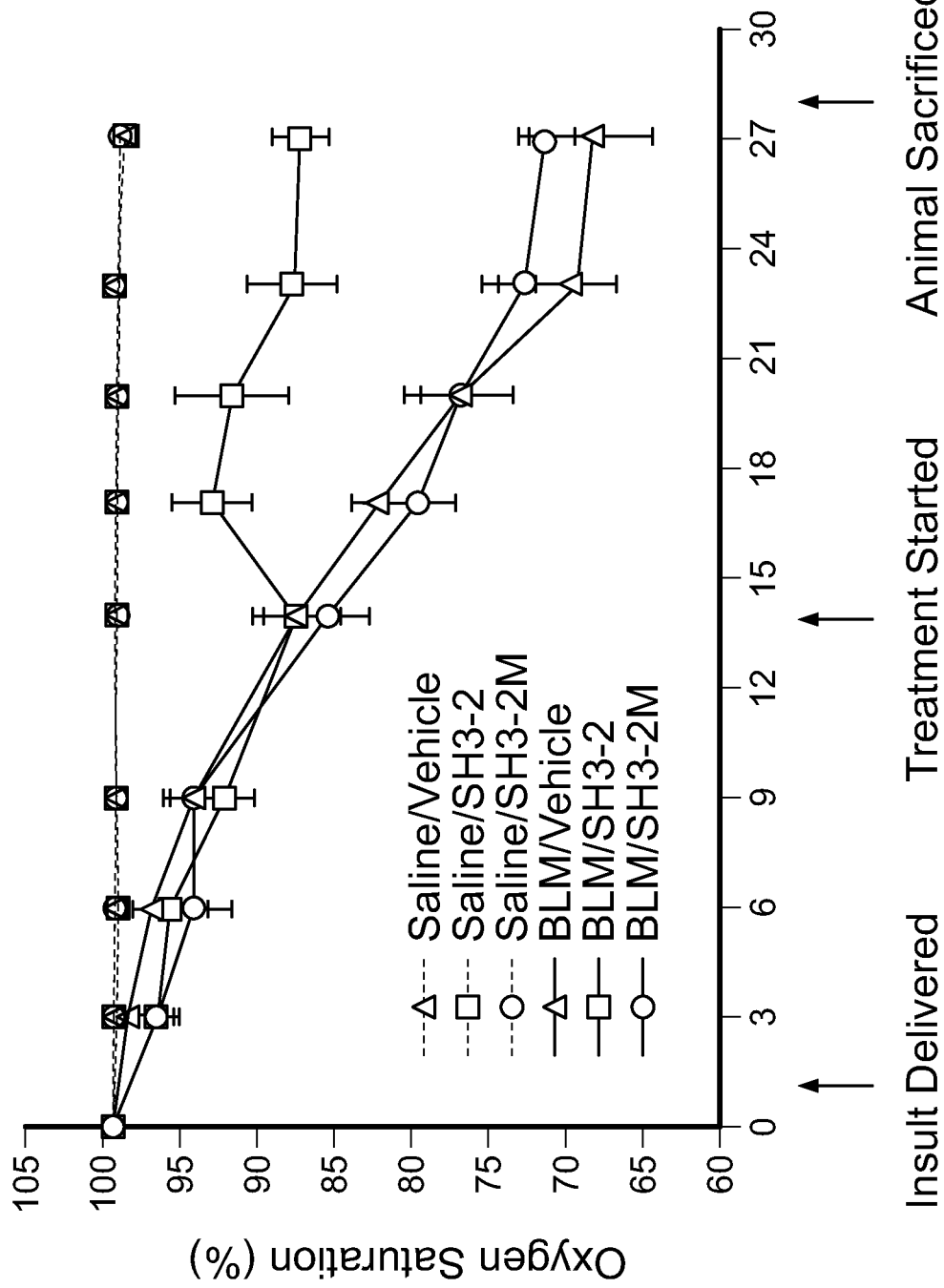
FIGS. 6A-6B. (A) Treatment with TAT-SH-2 stabilizes lung gas exchange in BLM-challenged mice. Time-dependent fluctuation of oxygen saturation ($SpO_2$) levels (determined on room air) in mice challenged with BLM (or saline) for 28 days and treated 1×/day with vehicle (methocel/saline), 0.5 mg/kg of TAT-SH3-2 or TAT-SH3-2M beginning 14 days after initial BLM insult. Error bars reflect SEM from n=4. (B) Time-dependent fluctuation of oxygen saturation ($SpO_2$) levels (determined on room air) in mice challenged with BLM (or saline) for 28 days and treated 1×/day with vehicle (methocel/saline) or the indicated concentration of TAT-SH3-2 or TAT-SH3-2M beginning 14 days after initial BLM insult. Error bars reflect mean+/−sd from n=5. *P<0.05, **P<0.01.
Figure 6B:
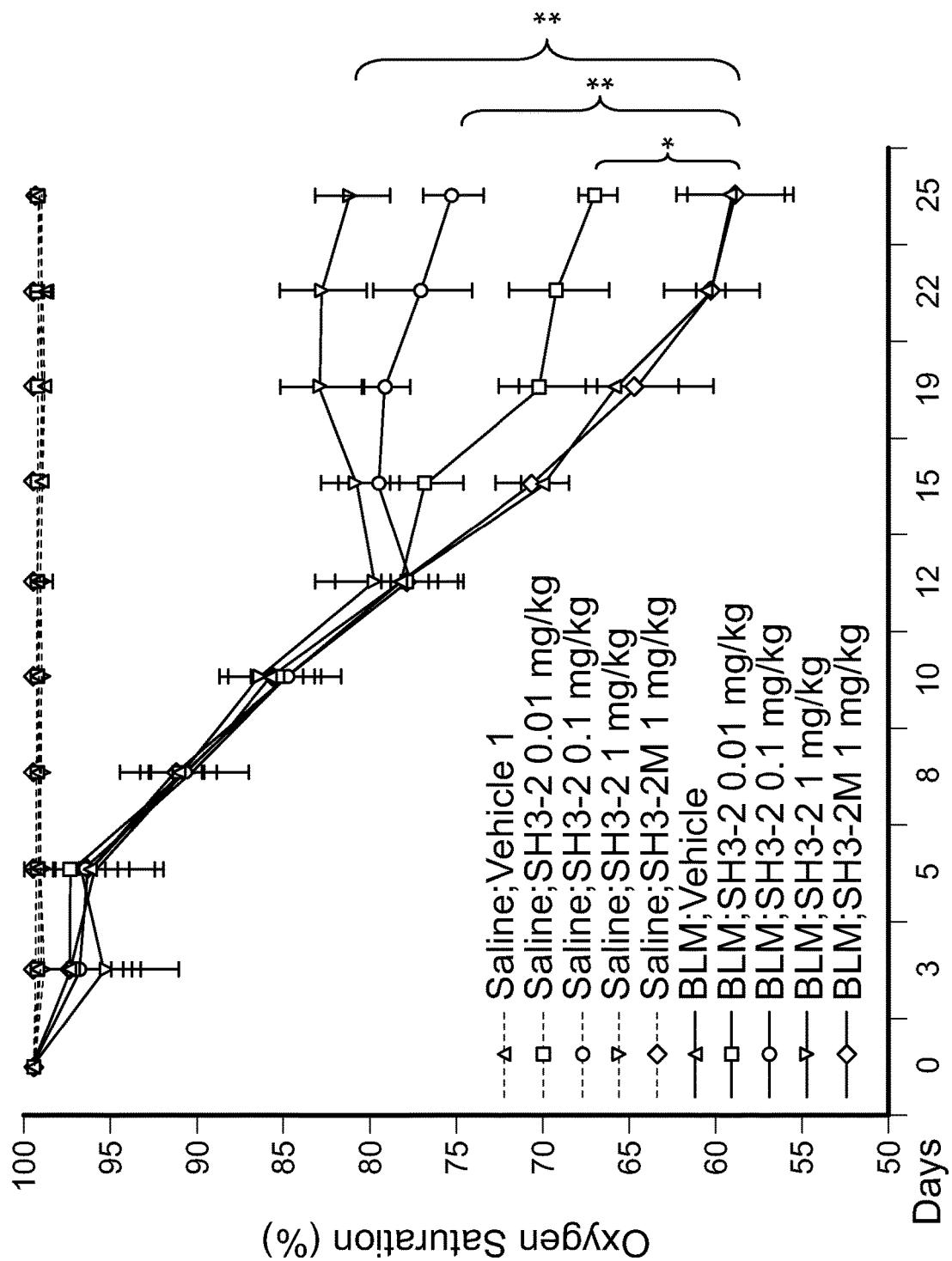
Figure 7:
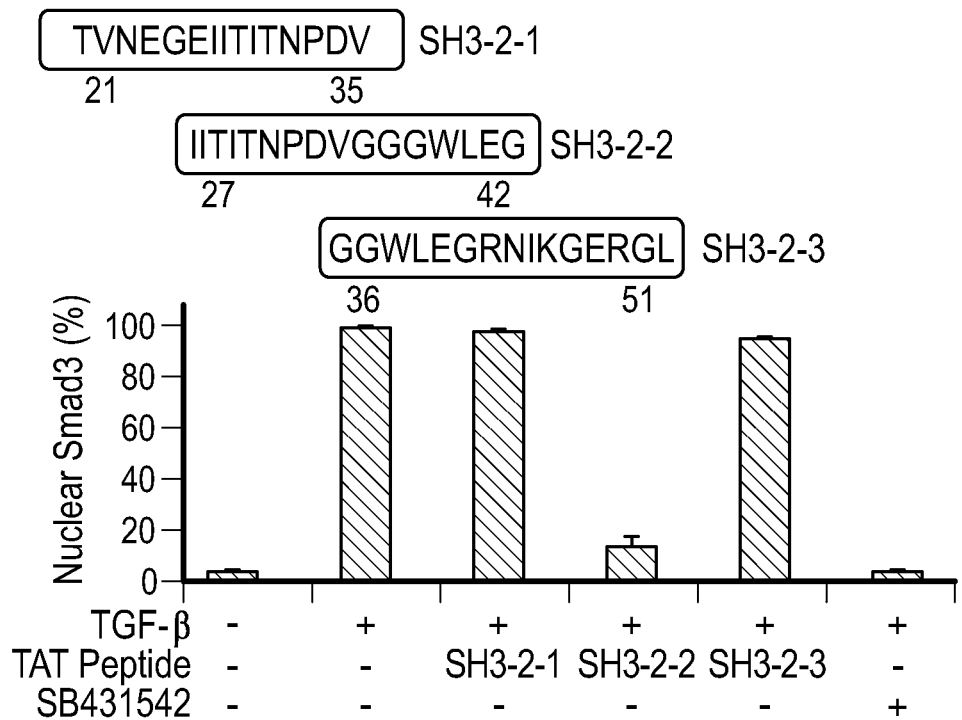
FIG. 7 contains a schematic of three overlapping polypeptides (SH3-2-1 (SEQ ID NO:33); SH3-2-2 (SEQ ID NO:34); and SH3-2-3 (SEQ ID NO:35)) used to further define the active motif in SNX9 (top). AKR-2B cells were transduced with the indicated TAT-SNX9(SH3) fusion polypeptides, and nuclear Smad3 staining was determined as in FIG. 1C. Data reflect nuclear Smad3 from 30 cells in each of two experiments (+/−SEM).

The results provided herein demonstrate that TAT-SNX9 (SH3) fusion polypeptides can prevent pSmad3 nuclear import and can function as an inhibitor of profibrotic TGFβ action both in vitro and in vivo. The following was performed to determine whether a corresponding improvement in lung physiology also is observed. This was directly examined by assessing the effect of TAT-SH3-2 (and TAT-SH3-2M) on peripheral blood oxygen saturation ($SpO_2$). Although an analogous decline in $SpO_2$ was observed in animals receiving the control TAT-SH3-2M polypeptide as those treated with saline, TAT-SH3-2 stabilized and/or improved gas exchange over the 2-week treatment interval (FIG. 6A). While vehicle or SH3-2M (the inactive TAT-SNX9 peptide) treated animals showed an approximate 25% decrease in $SpO_2$ during the treatment regime, a dose-dependent improvement in gas exchange was observed with TAT-SH3-2 such that animals receiving the highest concentration displayed no additional loss of lung function (FIG. 6B). Thus, by inhibiting pSmad3 action, a parameter of normal lung function was maintained.

Example 2—the Effect of a TAT-SNX9(SH3) Fusion Polypeptide on Subsynovial Connective Tissue Fibrosis in Carpal Tunnel Syndrome (CTS)

Fibroblasts were harvested from CTS patient SSCT tissue (n=3) who had carpal tunnel release surgery as described elsewhere (Gingery et al., *J. Orthop. Res.*, 32(11):1444-50 (2014)). The CTS SSCT fibroblasts were cultured in Minimum Essential Media (MEM) supplemented with 10% fetal bovine serum (FBS) and 1% antibiotic/antimycotic. Cultures were incubated at 37° C. in a humidified, 5% $CO_2$ atmosphere. 2 million cells per 6 well plate were cultured overnight. 24 hours later, the media was aspirated, and the cells were cultured in serum depleted media (0.5% FBS). Cultures were pretreated with TAT-SH3-2 (1.5 μM), TAT-SH3-2M, or vehicle for 90 minutes. Cell cultures were treated with 2 ng/mL TGF-β for 24 hours.

Total RNA was isolated gene expression was evaluated using quantitative real-time polymerase chain reaction (qRT-PCR) as described elsewhere (Gingery et al., *J. Orthop. Res.*, 32(11):1444-50 (2014)). TGF-β responsive genes (connective tissue growth factor (CTGF) and plasminogen activator inhibitor-1 (PAI-1)) were evaluated with TATA binding protein as the housekeeping gene.

Statistical analysis of qRT-PCR gene expression was normalized to control, and significance was determined by unpaired Student's t-test for each gene. The level of statistical significance is set at P<0.05.

Results

Figure 8:
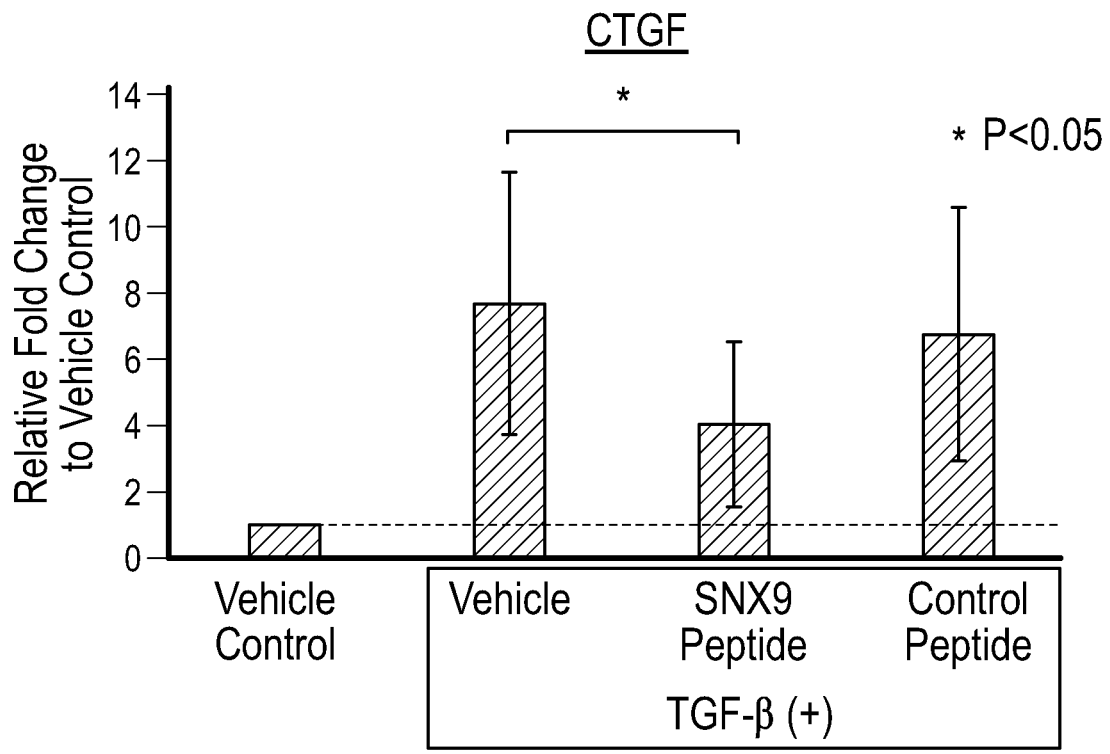
FIG. 8 is a graph plotting the expression of CTGF. TGFβ stimulated CTGF gene expression was examined in subsynovial connective tissue as in FIGS. 3D and 4B following addition of TAT-SH3-2 (SNX9 peptide) or TAT-SH3-2M (Control peptide). The results were normalized to control treatments without TGFβ.
Figure 9:
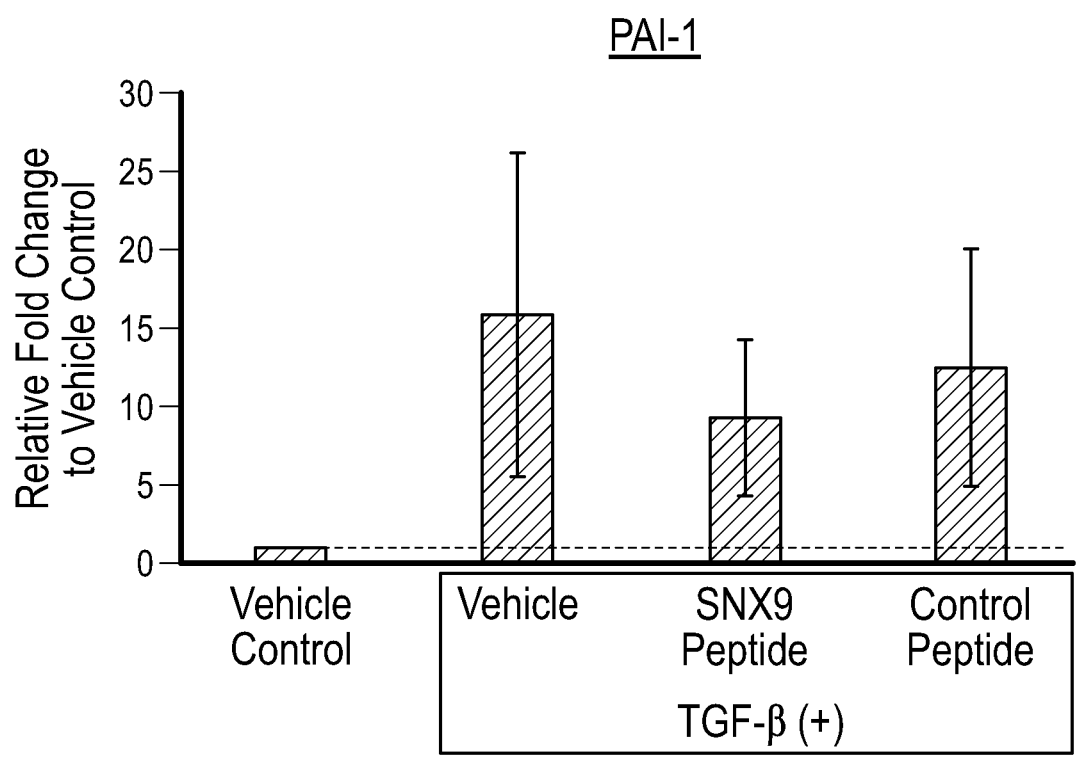
FIG. 9 is a graph plotting the expression of PAI-1 by cells exposed to the indicated treatments. TGFβ stimulated PAI-1 gene expression was examined in subsynovial connective tissue as in FIG. 8.

CTGF gene expression was down regulated by TAT-SH3-2 compared with vehicle (P<0.05; FIG. 8). No significant differences were observed between the three groups with respect to the expression of PAI-1. However, there is a substantial trend toward reduced expression (FIG. 9).

These results demonstrate that TAT-SNX9(SH3) fusion polypeptide can be used to attenuate TGF-β mediated gene expression of genes such as CTGF and PAI-1. Targeted blocking of Smad3 signaling as described herein can be used to treat CTS.

Example 3—RNAi to Treat Lung Fibrosis

A human is identified as having a fibrotic disease such lung fibrosis. Once identified, the human is administered (e.g., intravenously) a composition having one or more than one siRNA (and/or shRNA) designed to target SNX9 nucleic acid and trigger RNA interference against SNX9 nucleic acid expression. The composition is administered in an amount that delivers between about 5 µg/kg and 1500 µg/kg of siRNA (or shRNA) to the human. Once administered, the human is monitored to confirm a reduction in the severity of the lung fibrosis via imaging (e.g., CT scan) or lung function tests. Repeat doses of the composition are administered as needed. In such cases, the amount of the subsequent doses can be lower or higher than the initial dose to achieve a desired outcome.

Example 4—RNAi to Treat Liver Fibrosis

A human is identified as having a fibrotic disease such liver fibrosis. Once identified, the human is administered (e.g., intravenously) a composition having one or more than one siRNA (and/or shRNA) designed to target SNX9 nucleic acid and trigger RNA interference against SNX9 nucleic acid expression. The composition is administered in an amount that delivers between about 5 µg/kg and 1500 µg/kg of siRNA (or shRNA) to the human. Once administered, the human is monitored to confirm a reduction in the severity of the liver fibrosis via biopsy and/or non-invasive tests (e.g., elastography). Repeat doses of the composition are administered as needed. In such cases, the amount of the subsequent doses can be lower or higher than the initial dose to achieve a desired outcome.

Example 5—RNAi to Treat Kidney Fibrosis

A human is identified as having a fibrotic disease such kidney fibrosis. Once identified, the human is administered (e.g., intravenously) a composition having one or more than one siRNA (and/or shRNA) designed to target SNX9 nucleic acid and trigger RNA interference against SNX9 nucleic acid expression. The composition is administered in an amount that delivers between about 5 µg/kg and 1500 µg/kg of siRNA (or shRNA) to the human. Once administered, the human is monitored to confirm a reduction in the severity of the kidney fibrosis via biopsy and/or non-invasive tests (e.g., elastography). Repeat doses of the composition are administered as needed. In such cases, the amount of the subsequent doses can be lower or higher than the initial dose to achieve a desired outcome.

Example 6—TAT-SNX9(SH3) Fusion Polypeptides do not Inhibit In Vitro Cell Proliferation AKR-2B (10% DMEM/FBS) and MRCS (10% EMEM/FBS) cells were seeded at $2.5 \times 10^3$ or $1 \times 10^4$ cells/96 well plate, respectively. 24 hours after seeding, the medium was removed and replaced with DMEM or EMEM containing vehicle (0.1% DMSO), SH3-2 (1.5 µM), or SH3-2M (1.5 µM) either in 10% or 0.1% FBS for 24 hours prior to MTT assay. Absorbance was measured at 570 nm. In addition, AKR-2B ($1.25 \times 10^4$/well) or MRCS ($5 \times 10^4$/well) cells were seeded in 24 well plates for 24 hours. Cultures were treated with DMEM or EMEM containing vehicle (0.1% DMSO), SH3-2 (1.5 µM), or SH3-2M (1.5 µM) either in 10% or 0.1% FBS, and cell counts were determined following an additional 24 hours and 48 hours of incubation.

Figure 10A:
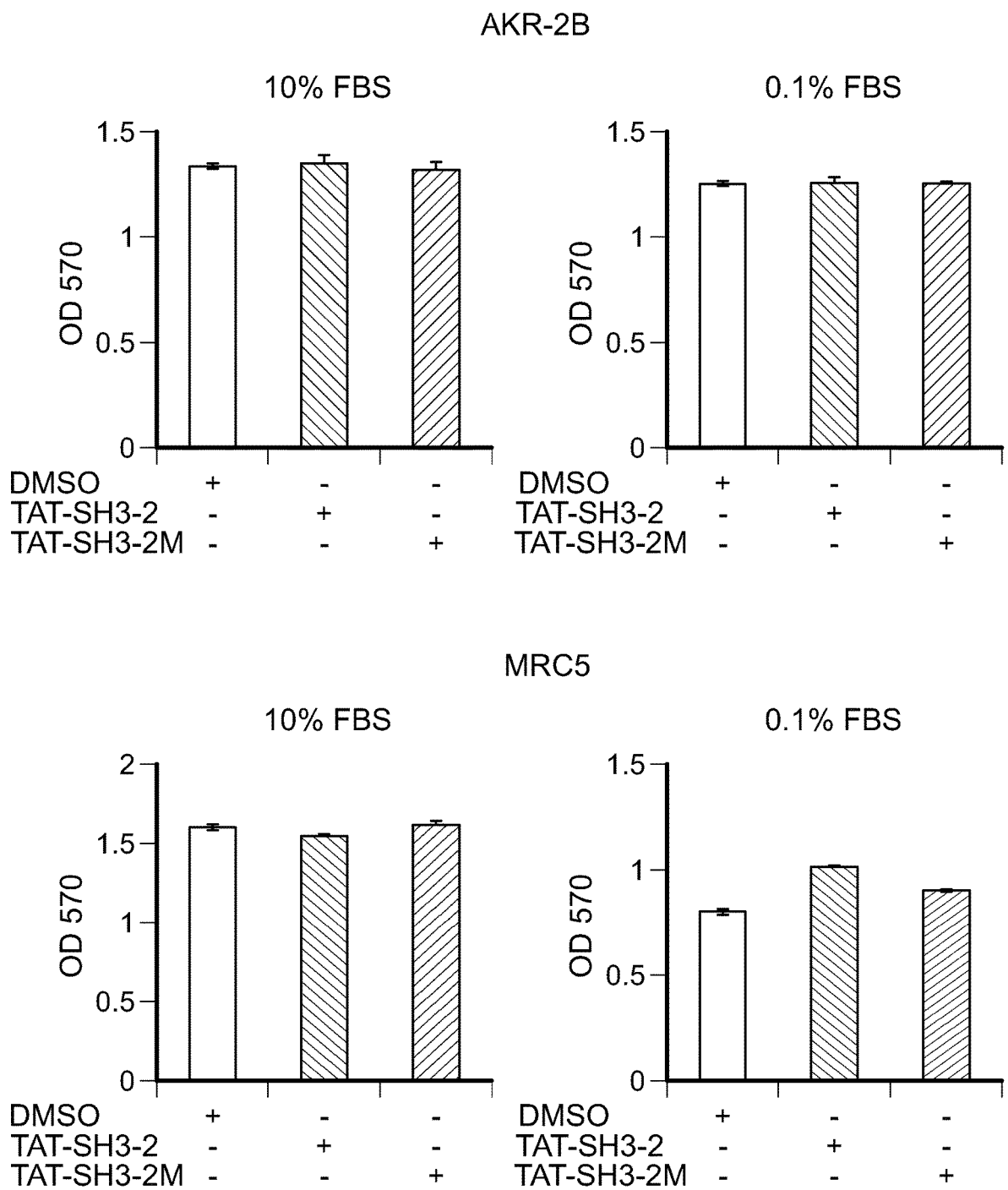
FIGS. 10A-10B contain graphs showing that TAT polypeptides do not inhibit in vitro cell proliferation. (A) AKR-2B (10% DMEM/FBS) and MRC5 (10% EMEM/FBS) cells were seeded at $2.5×10^3$ or $1×10^4$ cells/96 well plate, respectively. 24 hours after seeding, the medium was removed and replaced with DMEM or EMEM containing vehicle (0.1% DMSO), SH3-2 (1.5 µM), or SH3-2M (1.5 µM) either in 10% or 0.1% FBS for 24 hours prior to MTT assay. Absorbance was measured at 570 nm. (B) AKR-2B ($1.25×10^4$/well) or MRC5 ($5×10^4$/well) cells were seeded in 24 well plates for 24 hours. Cultures were treated as in FIG. 10A, and cell counts were determined following an additional 24 hours and 48 hours of incubation. Results represent mean±SEM from three independent experiments.
Figure 10B:
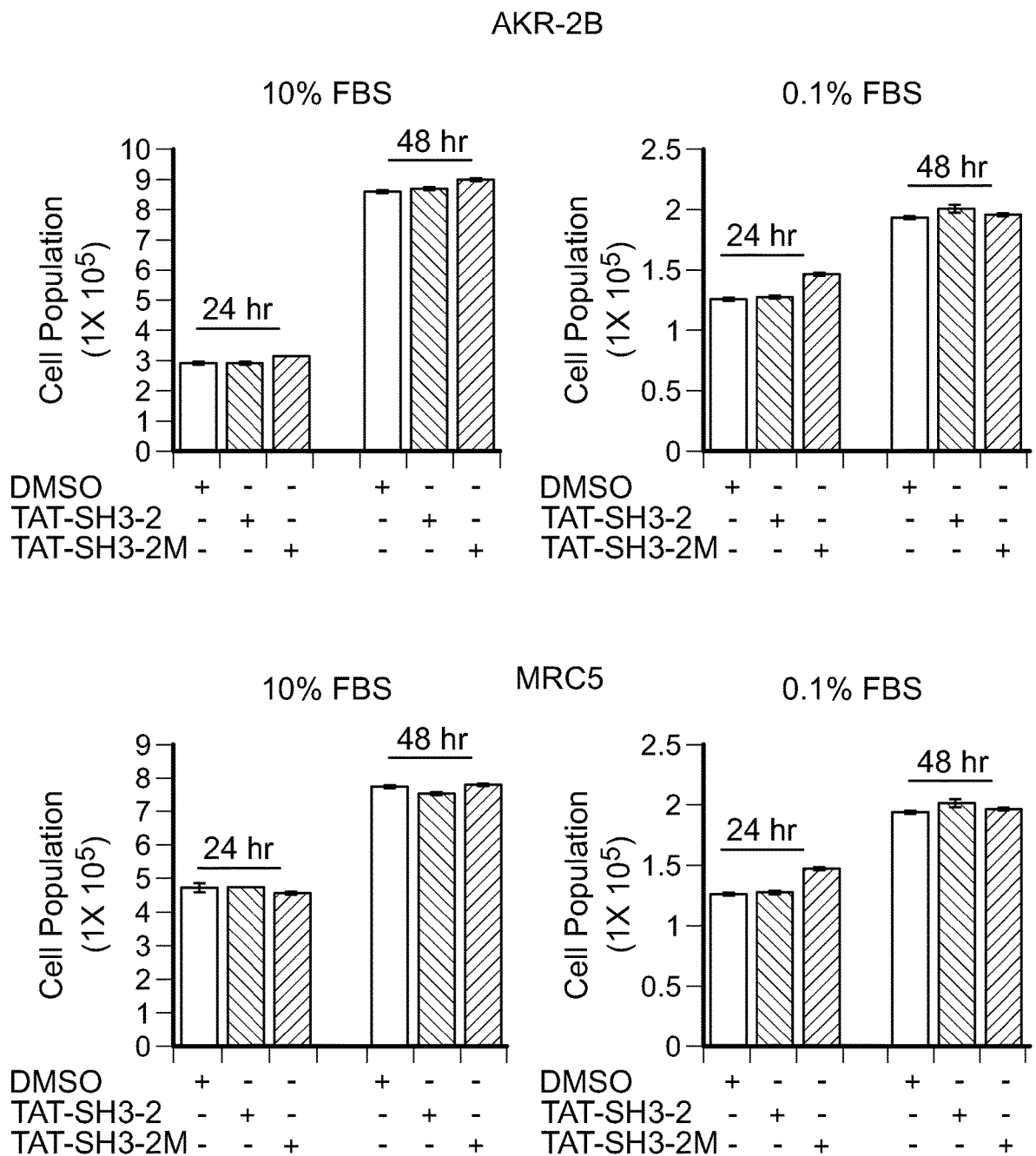

Exposure of cells to TAT-SNX9(SH3) fusion polypeptides did not inhibit cell proliferation (FIG. 10).

Example 7—TAT-SH3-2 Inhibits Profibrotic Responses in Human Lung Fibroblasts

Normal human lung fibroblasts (NHLF) or lung fibroblasts from idiopathic pulmonary fibrosis (IPF) patients were transduced with the indicated TAT polypeptide. TGFβ (5 ng/mL) or SB431542 (10 µM) was then added for an additional 24 hours. Images were obtained on a LSM510 confocal microscope following F-actin labeling with phalloidin-TRITC and DAPI nuclei staining. In addition, a Western analysis was performed for α-SMA (alpha smooth muscle actin), CTGF (connective tissue growth factor), and GAPDH (glyceraldehyde phosphate dehydrogenase) subsequent to TAT polypeptide transduction and 24 hour treatment in the absence or presence of TGFβ (5 ng/mL) or SB431542 (10 µM). Further, qPCR was performed using NHLF or IPF fibroblasts similarly treated.

Figure 11A:
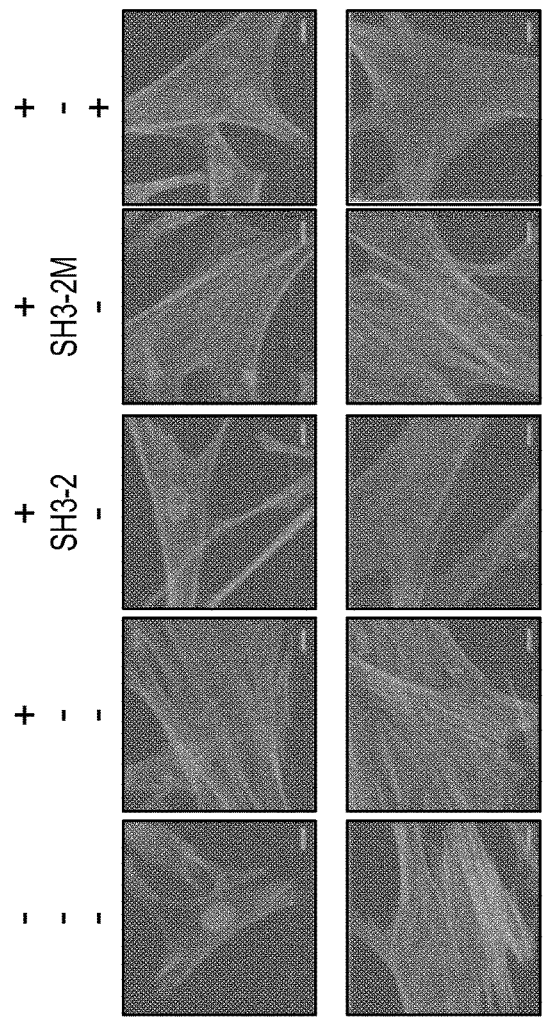
FIGS. 11A-11C. TAT-SH3-2 inhibits profibrotic responses in human lung fibroblasts. (A) Normal human lung fibroblasts (NHLF) or lung fibroblasts from idiopathic pulmonary fibrosis (IPF) patients were transduced with the indicated TAT polypeptide. TGFβ (5 ng/mL) or SB431542 (10 µM) was then added for an additional 24 hours. Images were obtained on a LSM510 confocal microscope following F-actin labeling with phalloidin-TRITC and DAPI nuclei staining. Scale bar: 10 µm. (B) Western analysis for the indicated polypeptides (α-SMA, alpha smooth muscle actin; CTGF, connective tissue growth factor; and GAPDH, glyceraldehyde phosphate dehydrogenase) subsequent to TAT polypeptide transduction and 24 hour treatment in the absence (−) or presence (+) of TGFβ (5 ng/mL) or SB431542 (10 µM). (C) NHLF or IPF fibroblasts were treated as in (A), and qPCR was performed as described herein. Results represent mean±SEM from three independent experiments. *P<0.05, P<0.005, * P<0.001.
Figure 11B:
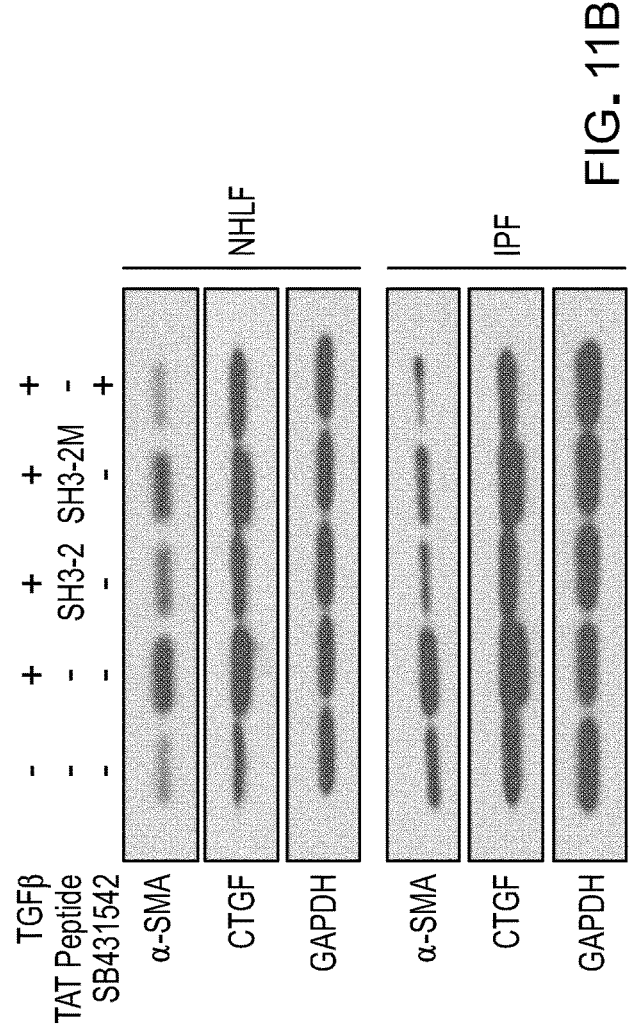
Figure 11C:
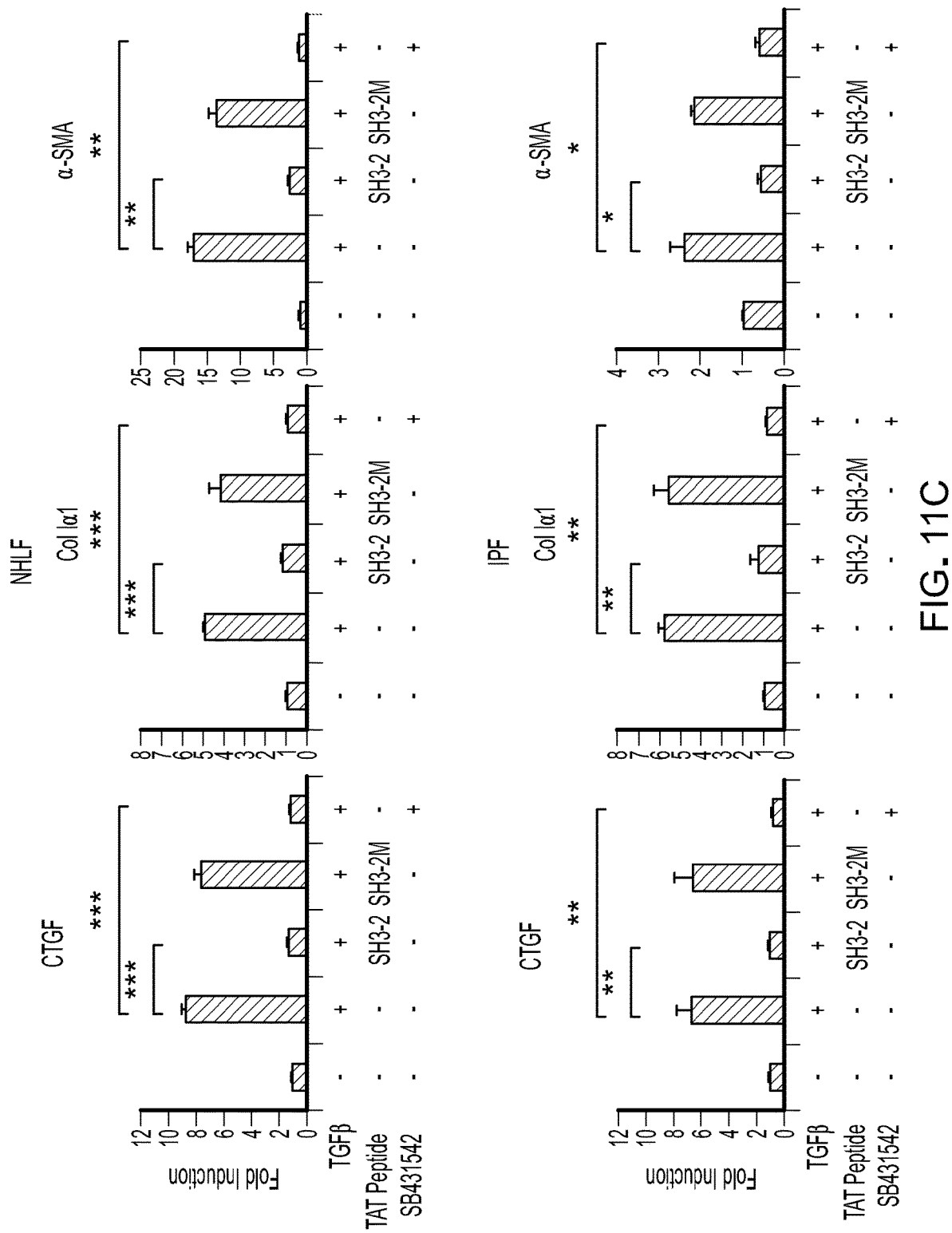

TAT-SH3-2 inhibited profibrotic responses in human lung fibroblasts (FIG. 11).

Example 8—TAT-SH3-2 has No Demonstrable Effect on Murine Liver Enzymes or Inflammatory Cell Recruitment C57BL/6 mice received intratracheal instillation of saline or bleomycin (BLM). On day 14, all animals began daily treatment with either vehicle (methocel/saline) or 1 mg/kg of TAT-SH3-2. Blood samples were obtained at days 0, 14, and 28 from the facial vein of unanesthetized animals and assessed for effect on the indicated liver enzymes and inflammatory cells. Quantification of lymphocytes, monocytes, and neutrophils were measured using a VetScan HM5 Analyzer. Serum levels (U/L, units per liter; g/dL, grams per deciliter) of alkaline phosphatase (ALP), alanine aminotransferase (ALT), and albumin were determined using a Piccolo Xpress Chemistry analyzer.

Figure 12:
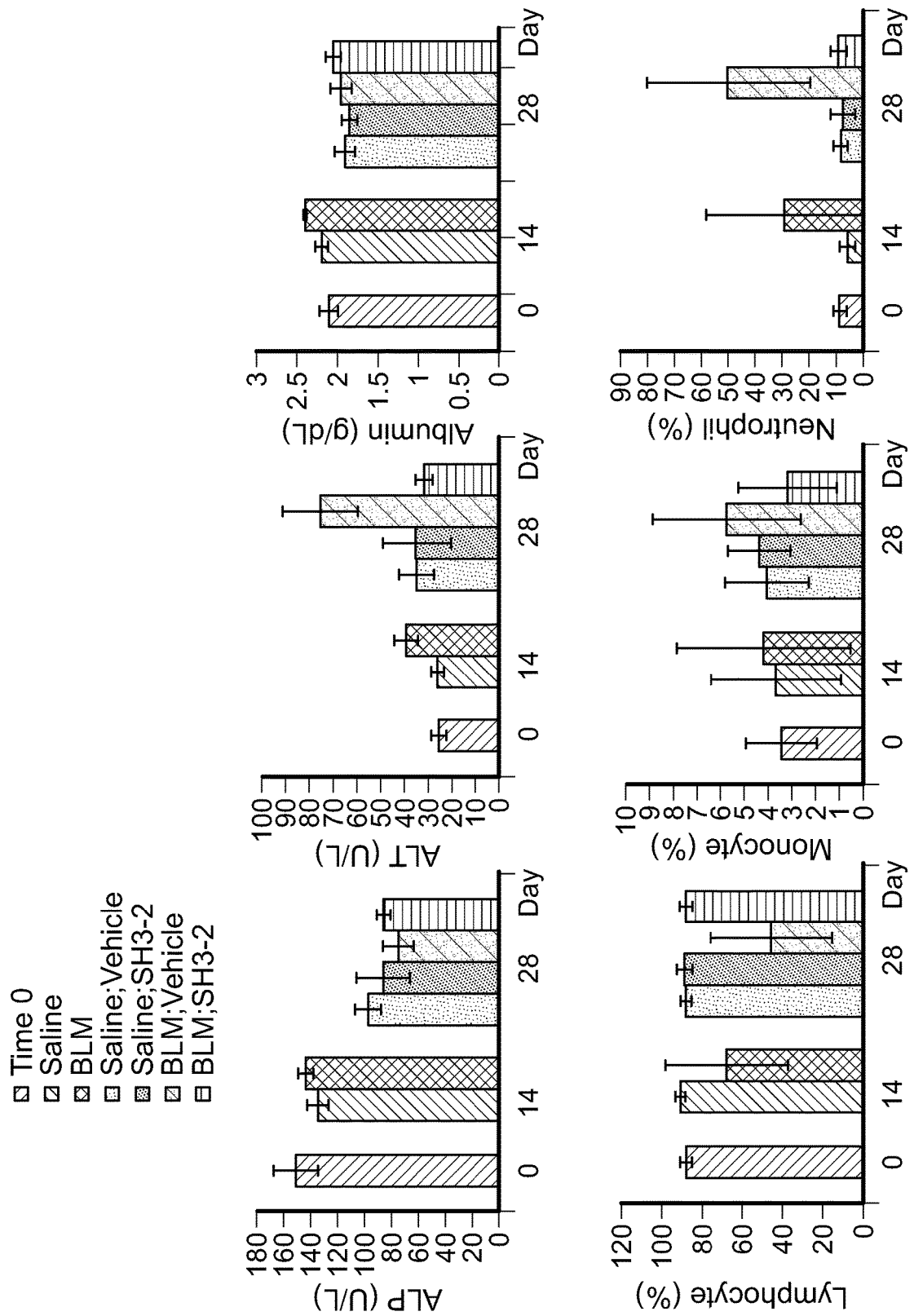
FIG. 12. C57BL/6 mice received intratracheal instillation of saline or bleomycin (BLM). On day 14, all animals began daily treatment with either vehicle (methocel/saline) or 1 mg/kg of TAT-SH3-2. Blood samples were obtained at days 0, 14, and 28 from the facial vein of unanesthetized animals and assessed for effect on the indicated liver enzymes and inflammatory cells. Quantification of lymphocytes, monocytes, and neutrophils were measured using a VetScan HM5 Analyzer. Serum levels (U/L, units per liter; g/dL, grams per deciliter) of alkaline phosphatase (ALP), alanine aminotransferase (ALT), and albumin were determined using a Piccolo Xpress Chemistry analyzer. Data are presented as mean+/−SEM of n=5.

TAT-SH3-2 exhibited no demonstrable effect on murine liver enzymes or inflammatory cell recruitment (FIG. 12).

Example 9—TAT-SH3-2 Stabilizes Lung Function in Adenovirus-TGFβ Models of Pulmonary Fibrosis Mice were infected with $1 \times 10^8$ pfu adenovirus particles expressing control (GFP) or active TGFβ by tracheal instillation. On day 21, all animals began daily treatment with either vehicle (methocel/saline) or 1 mg/kg of the indicated TAT polypeptide. On days 21 and 35, peripheral blood oxygen was determined. Mice were sacrificed on day 39 and processed for lung hydroxyproline content or qPCR expression of CTGF (connective tissue growth factor), α-SMA (alpha smooth muscle actin), and Col Iα1 (collagen Iα1).

TAT-SH3-2 stabilized lung function in adenovirus-TGFβ models of pulmonary fibrosis (FIG. 13).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid molecule encoding a polypeptide comprising a cell penetrating amino acid sequence and an amino acid segment of a SH3 domain of a sorting nexin 9 (SNX9) polypeptide, wherein said amino acid segment is less than 45 amino acid residues in length and comprises the amino acid sequence set forth in SEQ ID NO:6 or 7.

2. The nucleic acid molecule of claim 1, wherein said cell penetrating amino acid sequence comprises the amino acid sequence set forth in SEQ ID NO:2, SEQ ID NO:3, SEQ ID NO:4, or SEQ ID NO:5.

3. The nucleic acid molecule of claim 1, wherein said cell penetrating amino acid sequence comprises GYGRKKRRQRRRGS (SEQ ID NO:37).

4. The nucleic acid molecule of claim 1, wherein said polypeptide comprises the amino acid sequence set forth in any one of SEQ ID NOs:9, 11, 13-16, 18, 19, 21, 22, 24, and 25.

5. The nucleic acid molecule of claim 1, wherein said amino acid segment comprises the amino acid sequence set forth in SEQ ID NO:6.

6. The nucleic acid molecule of claim 1, wherein said amino acid segment comprises the amino acid sequence set forth in SEQ ID NO:7.

7. A host cell comprising a nucleic acid molecule encoding a polypeptide comprising a cell penetrating amino acid sequence and an amino acid segment of a SH3 domain of a sorting nexin 9 (SNX9) polypeptide, wherein said amino acid segment is less than 45 amino acid residues in length and comprises the amino acid sequence set forth in SEQ ID NO:6 or 7.

8. The host cell of claim 7, wherein said cell penetrating amino acid sequence comprises the amino acid sequence set forth in SEQ ID NO:2, SEQ ID NO:3, SEQ ID NO:4, or SEQ ID NO:5.

9. The host cell of claim 7, wherein said cell penetrating amino acid sequence comprises GYGRKKRRQRRRGS (SEQ ID NO:37).

10. The host cell of claim 7, wherein said polypeptide comprises the amino acid sequence set forth in any one of SEQ ID NOs:9, 11, 13-16, 18, 19, 21, 22, 24, and 25.

11. The host cell of claim 7, wherein said amino acid segment comprises the amino acid sequence set forth in SEQ ID NO:6.

12. The host cell of claim 7, wherein said amino acid segment comprises the amino acid sequence set forth in SEQ ID NO:7.

* * * * *